US010928411B2

(12) United States Patent
Hatamian

(10) Patent No.: US 10,928,411 B2
(45) Date of Patent: Feb. 23, 2021

(54) AUTOMATED MEDICAL SAMPLE COLLECTION AND TESTING

(71) Applicant: 2Pi-Sigma Corporation, Rancho Santa Margarita, CA (US)

(72) Inventor: Mehdi Hatamian, Mission Viejo, CA (US)

(73) Assignee: 2Pi-Sigma Corporation, Newport Beach, CA (US)

( * ) Notice: Subject to any disclaimer, the term of this patent is extended or adjusted under 35 U.S.C. 154(b) by 127 days.

(21) Appl. No.: 15/785,755

(22) Filed: Oct. 17, 2017

(65) Prior Publication Data

US 2018/0306831 A1 Oct. 25, 2018

Related U.S. Application Data

(60) Provisional application No. 62/488,174, filed on Apr. 21, 2017.

(51) Int. Cl.
*G01N 35/10* (2006.01)
*B01L 3/00* (2006.01)
(Continued)

(52) U.S. Cl.
CPC ........... *G01N 35/1079* (2013.01); *A61B 5/01* (2013.01); *A61B 5/02* (2013.01); *A61B 5/1455* (2013.01);
(Continued)

(58) Field of Classification Search
CPC ...................................................... A61B 5/15
See application file for complete search history.

(56) References Cited

U.S. PATENT DOCUMENTS

| 4,031,399 A | 6/1977 | Klein et al. | |
| 5,405,510 A * | 4/1995 | Betts | A61B 5/14539 204/403.02 |

(Continued)

FOREIGN PATENT DOCUMENTS

| WO | 2011029794 A1 | 4/2011 | |
| WO | 2016025843 A1 | 2/2016 | |
| WO | WO-2016025843 A1 * | 2/2016 | ............. A61B 5/157 |

OTHER PUBLICATIONS

"Particular." Merriam-Webster.com. 2020. merriam-webster.com. Mar. 2, 2020 (Year 2000).

*Primary Examiner* — Matthew D Krcha
(74) *Attorney, Agent, or Firm* — Genius Patent APC; Bruce Hare

(57) ABSTRACT

An automated fluid sample collector includes: a collection receptacle; an actuator; and a piercing element coupled to the actuator. An automated sample collection device includes: a sample receptacle; a needle that is able to extend into the sample receptacle; an actuator coupled to the needle such that the actuator is able to extend and retract the needle; and a fluid chip coupled to the sample receptacle, the fluid chip able to accommodate an amount of collected fluid. An automated method of collecting a fluid sample includes: activating a pump associated with a finger retention element in order to add fluid to the finger retention element; extending an actuator associated with a piercing element; opening a pinch valve; activating a collection pump; deactivating the collection pump; closing the pinch valve; and releasing fluid from the finger retention element.

11 Claims, 16 Drawing Sheets

(51) Int. Cl.
  *G01N 35/00* (2006.01)
  *A61B 5/01* (2006.01)
  *G01N 33/49* (2006.01)
  *A61B 5/157* (2006.01)
  *A61B 5/02* (2006.01)
  *A61B 5/151* (2006.01)
  *A61B 5/15* (2006.01)
  *A61B 5/1455* (2006.01)

(52) U.S. Cl.
  CPC ........ *A61B 5/157* (2013.01); *A61B 5/150022* (2013.01); *A61B 5/15194* (2013.01); *B01L 3/502* (2013.01); *B01L 3/502715* (2013.01); *B01L 3/502761* (2013.01); *G01N 33/49* (2013.01); *G01N 35/00732* (2013.01); *A61B 5/150068* (2013.01); *A61B 5/15087* (2013.01); *A61B 5/150099* (2013.01); *A61B 5/150175* (2013.01); *A61B 5/150221* (2013.01); *A61B 5/150229* (2013.01); *A61B 5/150358* (2013.01); *A61B 5/150412* (2013.01); *A61B 5/150503* (2013.01); *A61B 5/150854* (2013.01); *A61B 5/150946* (2013.01); *B01L 2200/0605* (2013.01); *B01L 2300/044* (2013.01); *B01L 2300/0627* (2013.01); *B01L 2300/0672* (2013.01); *B01L 2300/0864* (2013.01); *B01L 2400/043* (2013.01); *B01L 2400/0655* (2013.01); *G01N 2035/1062* (2013.01)

(56) References Cited

U.S. PATENT DOCUMENTS

| | | |
|---|---|---|
| 5,662,127 A | 9/1997 | Vaughn |
| 6,506,165 B1 * | 1/2003 | Sweeney ............... A61B 5/415 600/562 |
| 6,770,190 B1 | 8/2004 | Milanovski et al. |
| 7,374,949 B2 | 5/2008 | Kuriger |
| 8,413,886 B2 | 4/2013 | Creaven et al. |
| 2003/0067599 A1 | 4/2003 | Carrillo |
| 2003/0083685 A1 | 5/2003 | Freeman et al. |
| 2004/0173456 A1 | 9/2004 | Boos et al. |
| 2005/0032204 A1 | 2/2005 | Rodgers et al. |
| 2005/0105077 A1 | 5/2005 | Padmanabhan et al. |
| 2005/0123447 A1 | 6/2005 | Koike et al. |
| 2005/0208648 A1 | 9/2005 | Sage et al. |
| 2006/0068490 A1 | 3/2006 | Tang et al. |
| 2006/0228259 A1 | 10/2006 | Samsoondar |
| 2008/0194987 A1 * | 8/2008 | Boecker ............... A61B 5/1411 600/583 |
| 2008/0194988 A1 * | 8/2008 | Nakamura ........ A61B 5/14532 600/583 |
| 2008/0260542 A1 | 10/2008 | Nishikawa et al. |
| 2008/0297169 A1 | 12/2008 | Greenquist et al. |
| 2009/0269837 A1 | 10/2009 | Shevkoplyas et al. |
| 2009/0298097 A1 | 12/2009 | Harris et al. |
| 2010/0045267 A1 | 2/2010 | Dittmer et al. |
| 2010/0092470 A1 | 4/2010 | Bhatt et al. |
| 2010/0196207 A1 | 8/2010 | Steinmiller et al. |
| 2011/0137208 A1 * | 6/2011 | Valk ............... A61B 5/150358 600/583 |
| 2011/0201312 A1 | 8/2011 | Peterson et al. |
| 2012/0198921 A1 | 8/2012 | Lundgreen et al. |
| 2012/0208283 A1 | 8/2012 | Gheorghiu et al. |
| 2013/0004385 A1 | 1/2013 | Lee et al. |
| 2013/0158432 A1 | 6/2013 | Escutia et al. |
| 2013/0309778 A1 | 11/2013 | Lowe et al. |
| 2014/0058428 A1 | 2/2014 | Christopher et al. |
| 2014/0295433 A1 | 10/2014 | Chen et al. |
| 2014/0378800 A1 * | 12/2014 | Richter ............... A61B 5/1411 600/365 |
| 2015/0377814 A1 | 12/2015 | Schindelholz et al. |
| 2017/0016753 A1 * | 1/2017 | Shi ..................... G01F 22/00 |

* cited by examiner

AUTOMATED MEDICAL SAMPLE COLLECTION AND TESTING

CROSS-REFERENCE TO RELATED APPLICATIONS

This application claims priority to U.S. Provisional Patent Application Ser. No. 62/488,174, filed on Apr. 21, 2017.

BACKGROUND

Many users, whether professional or home-based, may wish to take blood samples (and/or other fluid samples) on a regular basis. For instance, people with type I diabetes may need to measure blood sugar at least four times per day.

Existing sampling methods require users to manually prick a fingertip to generate and collect a sample for testing. Such sampling results in inconsistent sample quantities, stress and anxiety for the subject, potential for sample contamination, and/or other issues related to manual collection and processing Furthermore, after generating a sample, a subject may need to perform additional operations such as collecting the sample, applying the sample to a test strip, inserting the strip into a testing device, etc.

Thus there is a need for a way to collect a measured sample using subject preferences to collect and process samples automatically.

SUMMARY

A sample collection and testing device (SCTD) of some embodiments may be able to collect a sample from a test subject. The SCTD may utilize removable cartridges. Such cartridges (or portions thereof) may be intended for single use.

Some embodiments are able to automatically collect a blood sample from a subject's finger. Such sample collection may involve detection of the subject (or finger in this example), piercing or pricking of the subject, collection, and/or storage of the sample. Although blood is used as one example, various other fluids may be collected and/or analyzed.

The sample may be collected via a receptacle (e.g., a recess in a surface of the cartridge) using a pump, valve, fluid sensing chip, tubing or other flow pathways, storage cavities, and/or other appropriate features.

A piercing element of some embodiments may include a needle and spring, actuator, and/or other appropriate elements. The piercing element may be automatically extended an appropriate amount to draw blood through the skin in this example. The amount of extension may be specified and/or limited in various appropriate ways (e.g., physical or mechanical barriers or stops, a value associated with the actuator extension, etc.). The extension may be set by a user, may be based on default values, or may be determined automatically using various sensors associated with the SCTD and/or cartridge.

In some embodiments, a fluid sensing device (and/or other elements of the cartridge) may include and/or be at least partially enclosed in a flexible material (e.g., silicone). Such enclosed elements may come into contact with the sample fluid and thus be intended to be single use or disposable. Other elements, such as the piercing element, that come into contact with the sample fluid may also be included in a disposable cartridge (or disposable portion thereof). Throughout the specification, any reference to "disposable" elements or components indicates single use components (e.g., components that will directly contact a blood sample).

Some embodiments may include non-contact sensing elements such that the fluid sensing device is able to be reused. Such non-contact elements may include, for instance, embedded sensors or leads that are able to be accessed via terminals along an outer surface of the cartridge. In some embodiments, the sensing elements may be able to sense properties of the sample through the enclosure without use of any exposed leads or contacts.

One example cartridge may be able to perform a test for cancer using human aspartyl (asparaginyl) β-hydroxylase (HAAH) protein and its associated antibodies. Such a cartridge may utilize magnetic beads and charge detection to evaluate samples.

Some embodiments of the SCTD (and/or associated cartridges) may be able to measure small amounts of fluid using optical components such as lasers to detect fluid within a transparent or semi-transparent fluid pathway.

The preceding Summary is intended to serve as a brief introduction to various features of some exemplary embodiments. Other embodiments may be implemented in other specific forms without departing from the scope of the disclosure.

BRIEF DESCRIPTION OF THE SEVERAL VIEWS OF THE DRAWINGS

The exemplary features of the disclosure are set forth in the appended claims. However, for purpose of explanation, several embodiments are illustrated in the following drawings.

DETAILED DESCRIPTION

The following detailed description describes currently contemplated modes of carrying out exemplary embodiments. The description is not to be taken in a limiting sense, but is made merely for the purpose of illustrating the general principles of some embodiments, as the scope of the disclosure is best defined by the appended claims.

Various features are described below that can each be used independently of one another or in combination with other features. Broadly, some embodiments generally provide an automated sample collection and testing device (SCTD).

A first exemplary embodiment provides an automated fluid sample collector comprising: a collection receptacle; an actuator; and a piercing element coupled to the actuator.

A second exemplary embodiment provides an automated sample collection device comprising: a sample receptacle; a needle that is able to extend into the sample receptacle; an actuator coupled to the needle such that the actuator is able to extend and retract the needle; and a fluid chip coupled to the sample receptacle, the fluid chip able to accommodate an amount of collected fluid.

A third exemplary embodiment provides an automated method of collecting a fluid sample, the method comprising: activating a pump associated with a finger retention element in order to add fluid to the finger retention element; extending an actuator associated with a piercing element; opening a pinch valve; activating a collection pump; deactivating the collection pump; closing the pinch valve; and releasing fluid from the finger retention element.

Several more detailed embodiments are described in the sections below. Section I provides a description of hardware architectures of some embodiments. Section II then describes various methods of operation of some embodiments. Lastly, Section III describes a computer system which implements some of the embodiments.

I. Hardware Architecture

Figure 1:
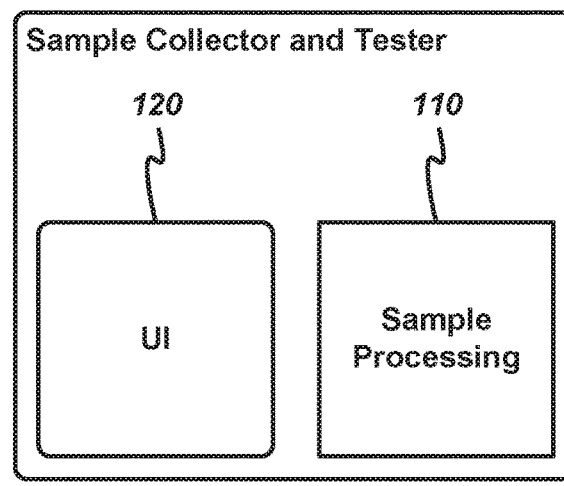
FIG. 1 illustrates a top view of an automated sample collection and testing device according to an exemplary embodiment.

FIG. 1 illustrates a top view of an automated SCTD 100 according to an exemplary embodiment. As shown, the device may include a removable test sample processing module 110, various user interface (UI) features 120, such as buttons, displays, touchscreens, keypads, LEDs, etc., and a housing 130.

The sample processing module 110 will be described in more detail in reference to FIG. 2 below. The housing 130 may be able to sit flat on a surface such as a tabletop or counter. The housing may include receptacles, sockets, etc. that may allow the housing to be attached to various elements, as appropriate (e.g., stands, carts, etc.). The housing may include various mechanical features (e.g., a cartridge release lever and associated mechanism, a hinged lid or door that provides access to elements within the housing, etc.).

Figure 2:
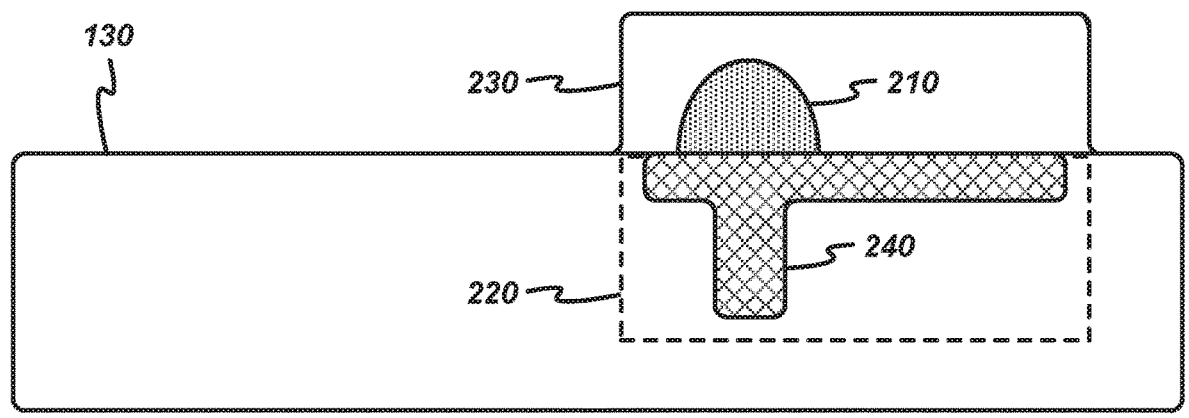
FIG. 2 illustrates a front elevation view of the automated sample collection and testing device of FIG. 1.

FIG. 2 illustrates a front elevation view of the automated sample collection and testing device 100. As shown, the sample processing module 110 of this example includes a receptacle 210 sized and shaped appropriately for a human finger, a bottom portion 220, a top portion 230, and a disposable cartridge 240 (or cavity if no cartridge has been inserted) that is able to be to be added to or removed from the sample processing module 110. In this example, the top portion 230 may include a hinge such that the top portion may be pulled away from the bottom portion to expose the cartridge 240 (or cavity).

Figure 3:
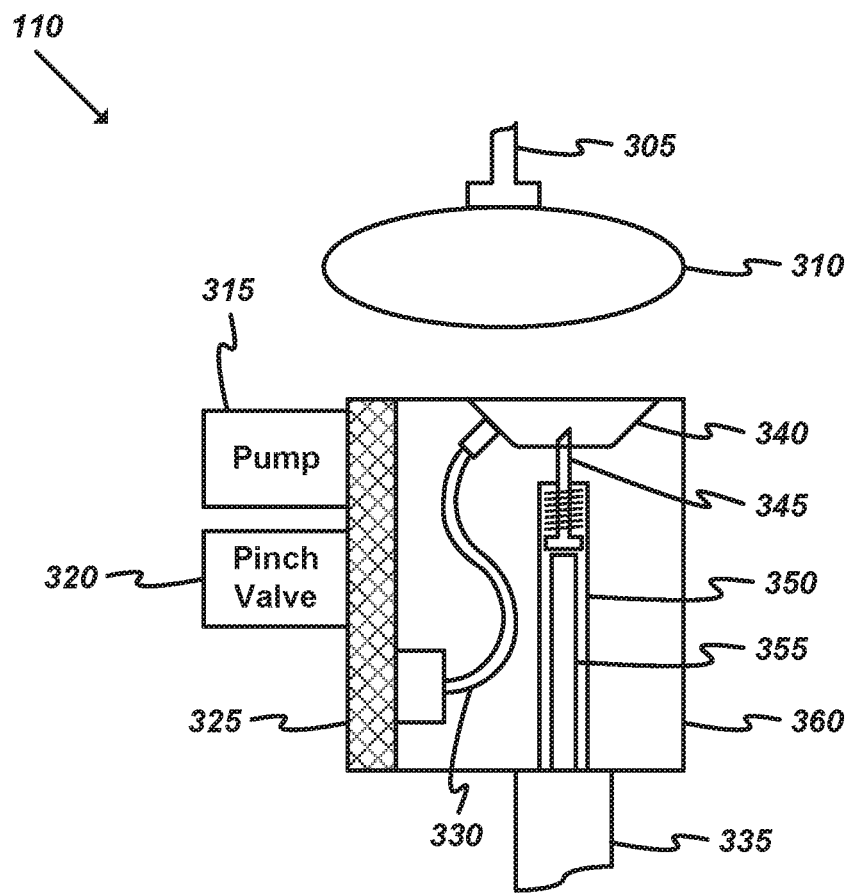
FIG. 3 illustrates a side elevation view of an exemplary embodiment of a sample processing module included in the sample collection and testing device of FIG. 1.

FIG. 3 illustrates a side elevation view of an exemplary embodiment of the sample processing module 110, showing various internal components of the cartridge. As shown, the cartridge may include a rubber pump 305, retention element 310, sample pump 315, pinch valve 320, chip 325, tubing or other connectors 330, an actuator 335, a receptacle 340, needle and spring 345, needle housing 350, needle connector 355, and cartridge housing 360.

In this example, elements 325-330 and 340-360 may typically be included in the disposable cartridge portion 240 of the sample processing module 110, while the other components may be included in a reusable portion of the sample processing module 110 or otherwise included in the SCTD 100.

The rubber pump 305 may be a device capable of pumping fluid (e.g., air) into the retention element 310. The fluid may be in a liquid and/or gaseous form. The retention element 310 may be a balloon or flexible bladder that is able to accept an appropriate amount of fluid and, in turn, provide adjustable resistance to pressure.

The sample pump 315 may be a pump capable of moving fluid along a pathway. In some embodiments, the sample pump may be associated with a measurement element or meter (not shown) that is able to determine an amount of fluid moved by the pump. The pinch valve 320 may be a controllable valve capable of permitting or restraining fluid flow within the sample processing module 110.

The "chip" 325 or fluid sensing plate may be able to store and/or interact with various fluids (e.g., sample fluids, reactants, catalysts, etc.). The chip may include electronic circuitry (e.g., sensors, integrated circuits, etc.) that may be able to detect or measure attributes of the fluid(s) and generate signals that provide the measured attributes to other components (e.g., a processor).

Some embodiments may include a fluid sensing plate that is reusable across multiple samples. Such a plate may either contact a sample indirectly (e.g., using disposable probes that are part of the cartridge and are able to provide electrical connection via some external connectors to the device 100). In some embodiments, the plate may be completely non-contact and sense fluid attributes through a silicone membrane or other appropriate cartridge material.

The tubing or other connectors 330 may allow fluid flow among the elements of the sample processing module 110.

In some embodiments, the tubing 330 may be formed by cavities within a solid element. For instance, in some embodiments, the chip 325, tubing 330, and receptacle 340 may be included in cube-shaped silicone.

The actuator 335 may be able to apply force to the connector 355. The actuator 335 may be able to extend and retract the connector 355. The actuator 335 may include components such as a linear solenoid, a rotary motor, etc. In some embodiments, the actuator may be controllable such that attributes such as depth or height, pressure, velocity, acceleration, torque, etc. may be able to be controlled based on various parameters (e.g., default values, user selections, measured values, etc.).

The receptacle 340 may include a recess or tub appropriate for placement of a finger in this example. Different embodiments may include different receptacles. For instance, some embodiments may include a connector that allows vials or other containers (e.g., micro tubes or other industry standard micro containers) to be coupled to the sample processing module 110. In some embodiments, the fluid may be collected and tested at the receptacle 340. For instance, a droplet of blood from a fingertip may be applied to a paper test strip located at the receptacle. In some embodiments, a micro tube or other container may be removed (after a sample has been collected) and sent elsewhere for testing (or attached to another testing device).

The extendable and retractable needle and spring 345 (or other piercing element such as a blade) may be able to extend out into the receptacle 340 such that a sample may be taken. The spring may cause the needle 345 to automatically retract when pressure is released from the actuator 335. The height and/or other attributes of the needle 345 may be adjusted manually or electronically (e.g., using actuators). For instance, some embodiments may include a physical knob that may allow users to adjust the height of housing 350, thereby controlling the maximum extension of the needle 345.

As another example, some embodiments may allow a desired height or extension of the needle 345 to be entered using a UI element or external device. Such desired height may be set in relative (e.g., discrete values from one to ten) or absolute terms (e.g., height in millimeters). The desired height may be used to control the operation of the actuator 335 to control the extension of the needle 345. Some embodiments may include various sensors that may automatically determine a desired height and apply such determined height to the operation of the needle 345. Such adjustment parameters may be stored such that a user may collect additional samples once comfortable needle use has been achieved.

The needle housing 350 may be a rigid hollow column. In this example, the housing is associated with a round needle and spring 345 and a cylindrical connector 355. Different embodiments may have elements with different shapes, based on the particular application.

The needle connector 355 may be a rigid member that couples the actuator 335 to the needle 345 such that the extension (or retraction) of the actuator 335 causes the needle 345 to be extended (or retracted).

The cartridge housing 360 in this example has a cube shape. The housing may include multiple portions. Some embodiments may include hinges, latches, etc. that may couple the portions. The housing may include various interfaces for use with the SCTD 100. Such interfaces may include, for instance, sockets or other connectors, terminals, wireless communication interfaces, etc.

During use, a subject's finger may be retained using the rubber pump 305 and balloon 310. The punching needle and associated spring 345 may be manipulated by the actuator 335 via the connector 355 to pierce the subject's finger and a blood sample may be collected using the chip 325, pinch valve 320, pump 315, and collection receptacle 340 under the finger. In addition, various tubes, connectors, etc. 330 may be utilized to transport fluid from the collection receptacle 340 to the chip 325.

The pressure of the balloon 310 (or other retaining element) may be adjustable. Such pressure may be set to retain the finger in place without causing a feeling that the finger is trapped or any other discomfort. Such a pressure adjustment may utilize various appropriate UI elements, including, for instance, up/down buttons, touchscreen features, received command from an external device, etc. Such adjustments may be stored for future use by a particular subject.

In this example, the sample processing module 110 includes automated collection and processing. Some embodiments may be able to receive a cartridge that includes a previously collected sample (e.g., held in a microtube). Such embodiments may be able to pierce (and/or otherwise interact with) the microtube in order to retrieve and analyze the collected sample.

Some embodiments may include at least one flowmeter. Such a flowmeter may follow the collection point in order to monitor the flow of fluid and/or measure volume. Such elements may be omitted in some embodiments in order to reduce cost of the sample processing module 110 (or disposable portions thereof).

In some embodiments, the SCTD 100 may automatically detect the finger and activate the device. Some embodiments may include a manual control such as a button or touchscreen 120 that can be used to activate the device 100. Such a control may be received as a command message from an external user device.

Figure 4:
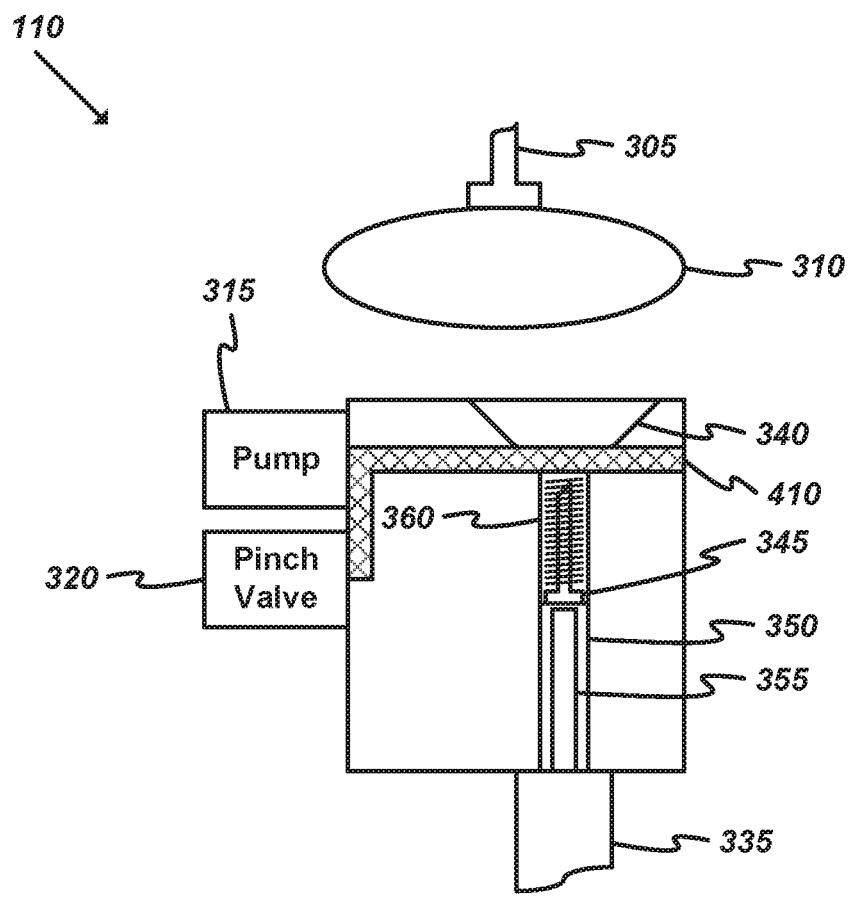
FIG. 4 illustrates a side elevation view of another exemplary embodiment of the sample processing module included in the sample collection and testing device of FIG. 1.

FIG. 4 illustrates a side elevation view of another exemplary embodiment of the sample processing module 110. In this example, the chip 410 may be located at the sample collection point (e.g., receptacle 340 where the finger is placed). The chip 410 may be made from a flexible material such as silicone. In such embodiments, the needle 345 may be placed below the chip 410 and pierce the chip 410 before pricking the finger. The material may then seal itself after the needle 345 is retracted such that the blood is retained within the chip or sample collection cavity 410. In this example, the needle 345 is in a fully retracted position whereas in the example of FIG. 3, the needle was in a partially or fully extended state.

In this example, the needle housing 350 may be split into two portions (a top portion and a bottom portion from this view), where one portion (i.e., the top portion in this example) is included in the disposable insert 360 of some embodiments. Other components may be included in the disposable insert, such as the needle and spring 345, the chip 410, and the receptacle 340. As above, any electronic sensing plate may be included in the removable cartridge 360 along with the chip 410 or may be included with the non-disposable components.

In the examples of FIG. 3 and FIG. 4, different embodiments may include different components within the disposable cartridge of some embodiments. Likewise, various different components may be included within the non-disposable elements of the device 100. Such components may be distributed among the disposable and non-disposable portions based on various relevant criteria (e.g., component cost, availability of components, cartridge footprint, device sensing capabilities, etc.).

Figure 5:
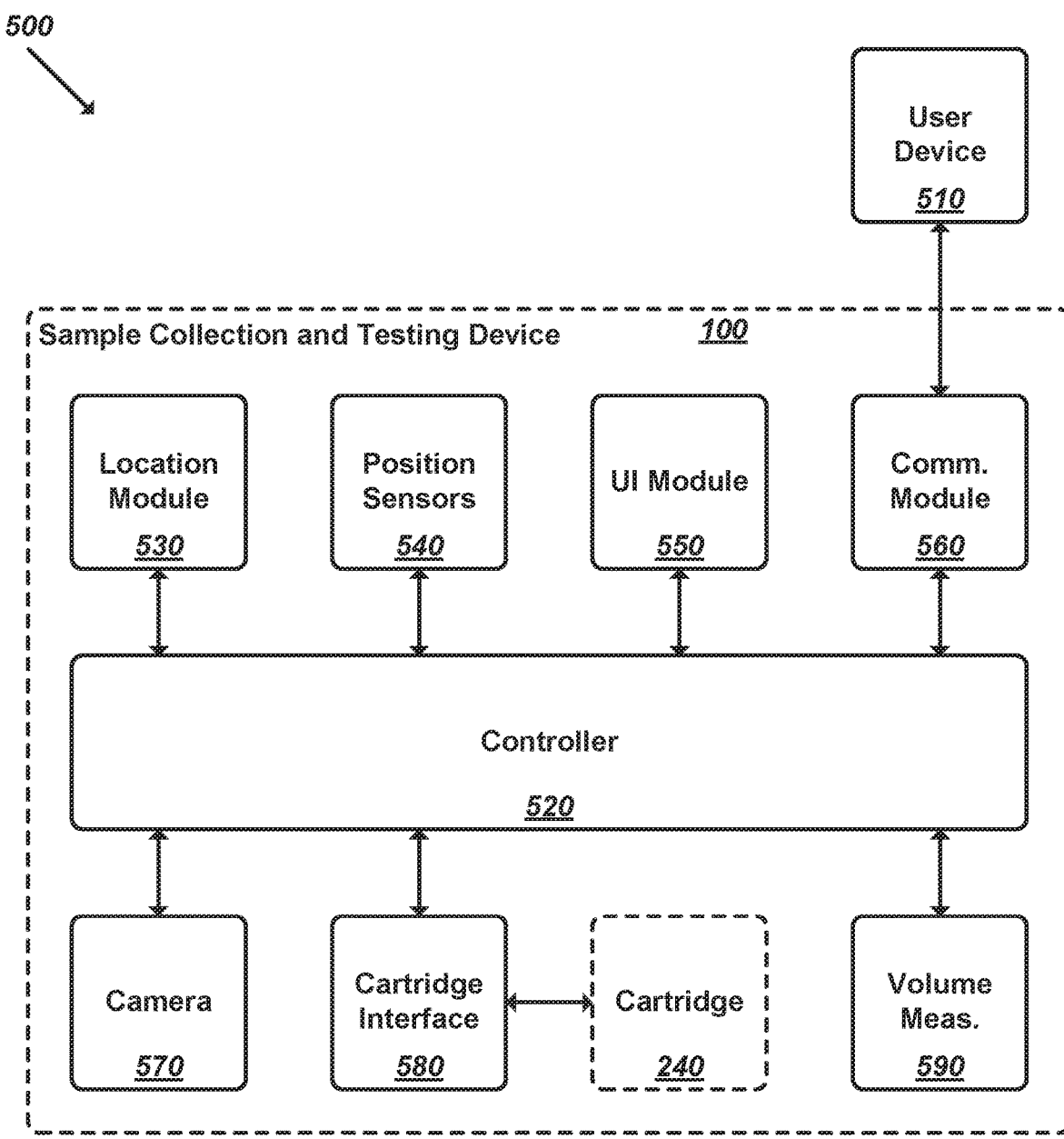
FIG. 5 illustrates a schematic block diagram of a system including the automated sample collection and testing device of FIG. 1.

FIG. 5 illustrates a schematic block diagram of a system 500 including the automated SCTD 100, sample processing module 110, and a user device 510. As shown, the SCTD 100 may include a controller 520, location module 530, position sensors 540, UI module 550, communication module 560, camera 570 (and/or other appropriate sensors), cartridge interface 580, and volume measurement module 590.

The sample processing module 110 may be similar to that described above in reference to FIG. 2, FIG. 3, and FIG. 4. The module 110 may include a removable test cartridge. The cartridge, or portions thereof, may be disposable (i.e., intended for a single use). several exemplary modules 110 will be described in more detail in reference to FIG. 6-FIG. 8 below.

The user device 510 may be an electronic computing device, such as a smartphone, tablet, personal computer, medical device, etc. The user device may provide various system features, such as UI output elements (e.g., display of test results, status, etc.), UI input elements (e.g., menus, buttons, etc.), and/or connectivity (e.g., via a cellular or wireless network connection). In some embodiments, the user device may be able to at least partly control the operations of the SCTD 100. For instance, a user such as a medical professional may initiate a test sequence by pressing a button on a tablet after a subject has been properly positioned with respect to the SCTD 100 (and sample collection element thereof).

The controller 520 may be an electronic device that is able to execute instructions and/or process data. The controller may be able to at least partly direct the operations of the other components. The controller may be associated with a local memory (not shown) that is able to store instructions and/or data.

The location module 530 may include various electronic components that are able to determine a geographic location. Such components may include, for instance, global positioning system (GPS) components.

The position sensors 540 may include various sensors, accelerometers, gyroscopes, etc. that may be able to determine a relative position of the SCTD. Such components may be used to ensure, for instance, that the SCTD is on a level surface. Some embodiments may include components that are able to automatically adjust device position based on such sensor measurements.

The UI module 550 may include various buttons, touchscreens, displays, indicators, keypads, microphones, speakers, etc. that may allow interaction with a user and/or subject.

The communication module 560 may be able to communicate across one or more wired or wireless pathways. Such pathways may include, for instance, universal serial bus (USB), Bluetooth, Wi-Fi, Ethernet, the Internet, etc.

The camera 570 (and/or other appropriate sensors) may be a color, HD camera that is able to capture video and/or still photographs. Such captured data may be able to be automatically analyzed by the controller and/or other components. Other embodiments may include different types of sensors such as environmental sensors (e.g., temperature, humidity, elevation, barometric pressure, etc.), subject attribute sensors (e.g., temperature, pulse rate, blood pressure, etc.), etc. In some embodiments, the sensors may be provided by one or more external components, with a resource such as controller 520, via communication module 560, may retrieve the data from such external components.

The cartridge interface 580 may include various components appropriate for interaction with a removable test sample processing module 110. For instance, some embodiments may utilize the camera 570 to scan a graphic code on the test cartridge. As another example, some embodiments may include components that are able to read radio frequency identification (RFID) tags or other similar tags. As still another example, some embodiments may be able to retrieve information through a digital or analog connection to the sample processing module 110. As yet another example, some embodiments may utilize near-field communication (NFC).

In some embodiments, the cartridge interface 580 and sample processing module 110 may have shared elements, complementary elements, and/or otherwise associated components that may together provide various functions described in reference to the cartridge.

The volume measurement module 590 may be able to interact with the cartridge interface 580 (and/or other appropriate elements) in order to determine volume measurements associated with sample fluids. As described in more detail in reference to FIG. 11 below, the volume measurement module 590 may include and/or interact with various other elements (e.g., optical sources and sensors) that are able to determine a volume of a fluid sample.

Figure 6:
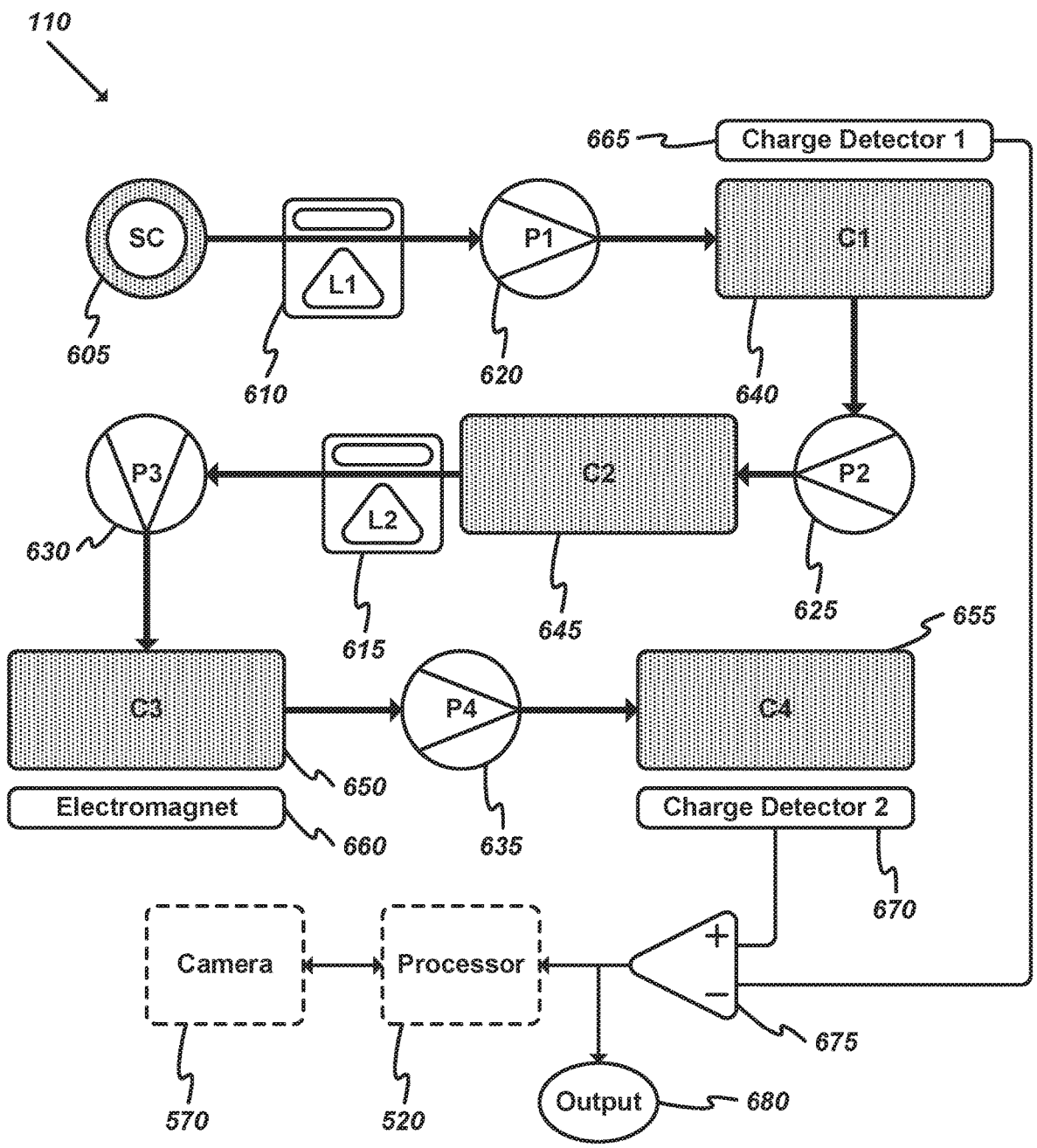
FIG. 6 illustrates a schematic block diagram of an exemplary embodiment of the sample processing module included in the sample collection and testing device of FIG. 1.

FIG. 6 illustrates a schematic block diagram of an exemplary embodiment of the sample processing module 110. As shown, this example module may include a sample collection element 605, multiple laser measurement elements 610-615, multiple bi-directional pumps 620-635, multiple cavities 640-655, an electromagnet 660, a pair of charge detectors 665-670, a differential output generator 675, a camera 570, and a processor 520. This example sample processing module 110 is associated with tests to diagnose cancer. Different embodiments may include different components and/or arrangements of components when associated with other tests (e.g., blood sugar levels).

The sample processing module 110, or portions thereof, may be self-contained such that each subject may use a new disposable cartridge. As such, the fluid collected by the cartridge may be completely contained within the cartridge and not exposed to the SCTD device 100. The cartridge elements may be made out of (and/or enclosed or embedded in) appropriate materials that are impervious to the various fluids collected or used within the sample processing module 110. Such materials may include plastics, silicone, composites, etc. In this example, the fluid flow pathway is indicated by thicker arrows, while communicatively coupled elements are indicated by thinner lines or arrows. In addition, the components that contact the sample are indicated by a fill pattern.

In some embodiments, the disposable cartridge portion may include the sample collection element 605, the cavities 640-655, and the tubing between them. Such a configuration allows the more expensive components (such as pumps, laser detectors, etc.) to be reused across multiple cartridges.

The sample collection element 605 may be similar to that described above in reference to FIG. 3 or FIG. 4. At minimum, the sample collection element may include a cavity that is able to receive an amount of fluid for testing. In some embodiments, the cavity may include a fluid sensing chip. Some elements of the sample collection element (e.g., the pump or pinch valve) may be shared with other elements of the sample processing module 110. For instance, pump 620 may act as pump 315 in some embodiments.

Each of the pumps 620-635 may be a peristaltic or other appropriate pump that is able to move fluid along a flow pathway (e.g., the areas indicated by the fill and thick arrows). Such a pathway may include various flexible tubes or cavities within a fluid retaining housing (e.g., a silicone housing). In some embodiments, a peristaltic pump may move fluid along the pathway. Such pumps may also act as valves, such that when the pumps are not operating, fluid flow between cavities (and/or other elements along the pathway) is prevented.

Each of the multiple laser measurement elements 610-615 (or other optical sensors, or other types of volume measurement sensors) may include a source and a collector or absorber. The laser measurement elements may be placed along the fluid flow pathway such that fluid flow is able to be detected. The optical sensors 610-615 of some embodiments may be utilized without contacting the fluid sample. In this way, the cost of cartridges may be reduced as the sensors are able to be used across numerous samples.

Each of the multiple cavities 640-655 may be able to store an appropriate amount of fluid. The cavities may be connected to the flow pathway at multiple locations (e.g., an input and an output).

The electromagnet 660 may include various appropriate components that are able to provide a controllable magnet.

The pair of detectors 665-670 (e.g., charge detectors, impedance detectors, conductivity detectors, etc.) may include various elements such as metal plates, capacitors, circuitry, etc. that may be able to detect and/or store charge, and/or otherwise sense qualities of the cavity contents.

The differential output generator 675 may be able to receive the outputs of the charge detectors 665-670 and generate a signal 680 that is proportional to a difference in sensed charge at each charge detector 665-670. The differential output 680 may be provided as an analog and/or digital signal. The output may be provided to a processor 520, as shown, and/or may be provided directly to an external resource such as the SCTD 100.

The camera 570 may be able to capture images and/or video associated with the sample processing module 110. The camera 570 may be placed above the sample processing module 110 such that activity inside the cartridge may be monitored. The camera 570 may be able to track fluid movement (and/or other appropriate factors) in real time such that adjustments may be made or problems identified. In some embodiments, the camera may be associated with the SCTD 100 rather than included in the disposable cartridge in order to reduce cartridge cost. The camera 570 may be high definition, 4K, and/or other appropriate formats of any resolution. Higher resolutions may provide more image processing capability if needed.

The processor 520 may be an electronic device capable of executing instructions and/or processing data. The processor may be able to at least partly control the operations of the various other components (although various connections have been omitted for clarity). For instance, the processor may direct the operations of the electromagnet 660. As another example, the processor 520 may receive and analyze data from the laser measurement elements 610-615. The processor 520 may have an associated memory (not shown).

Although this example includes charge detectors 665-670 and an electromagnet 660 that are used for charge differential detection, other embodiments may utilize other sensing components. For instance, some embodiments may include active electronic components such as sensors that directly contact the fluid sample. In such cases, a signal from such a component may be received and analyzed by the processor 520 of some embodiments (and/or other appropriate components such as a sensor interface). Some embodiments may utilize inductive power and wireless data exchange such that no physical connections to the chip are needed.

Figure 7:
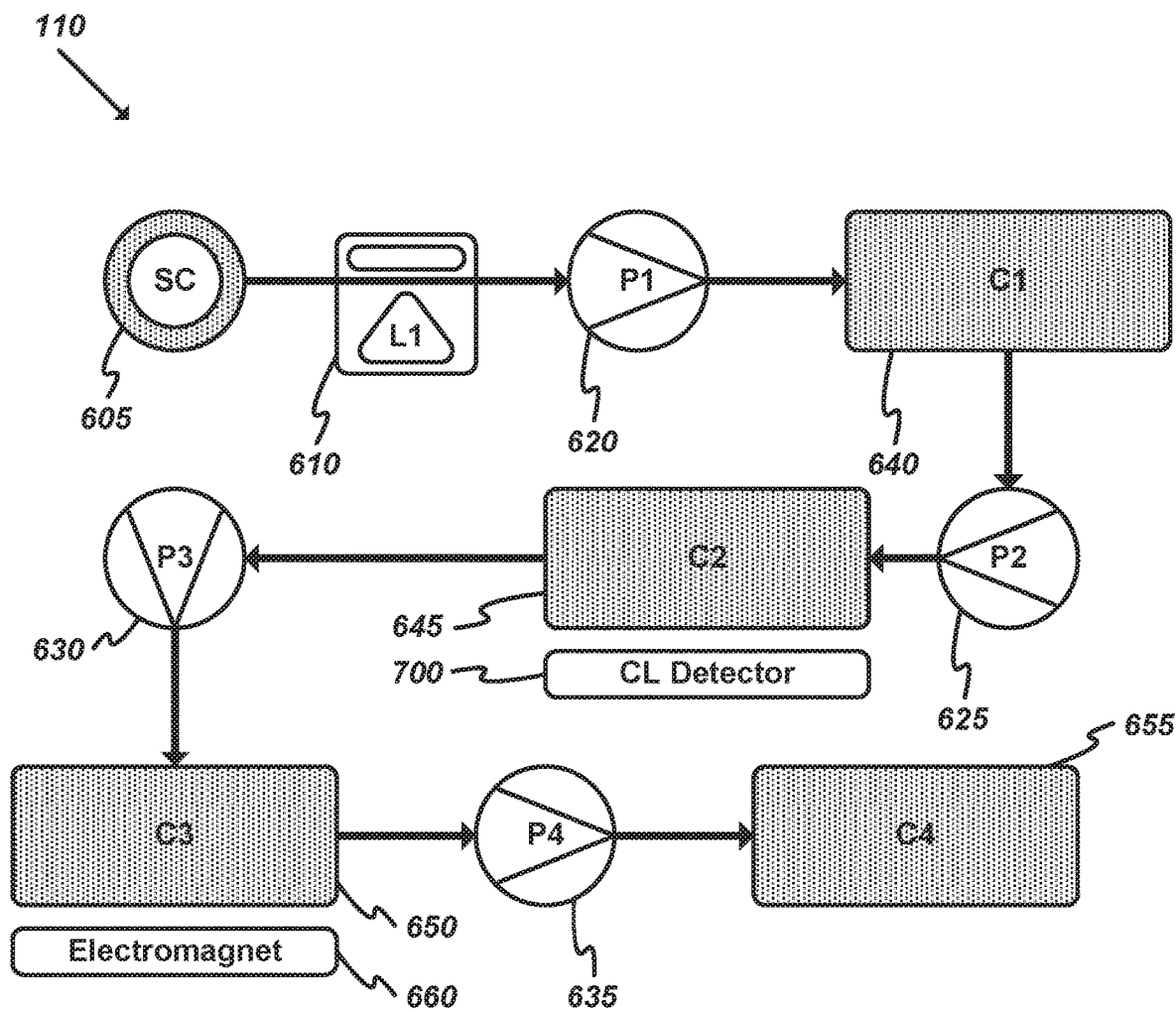
FIG. 7 illustrates a schematic block diagram of a second exemplary embodiment of the sample processing module included in the sample collection and testing device of FIG. 1.

FIG. 7 illustrates a schematic block diagram of a second exemplary embodiment of the sample processing module 110. As shown, the module may include many of the same components as the module of FIG. 6. In the example of FIG. 7, the second cavity 645 may be associated with a chemiluminescence (CL) detector 700. Such a detector may be able to sense photons emitted from CL particles. In addition, unlike the example of FIG. 6, the charge detectors 665-670 and second measurement element 615 are not needed. The output of the CL detector 700 may be converted to a discrete value and supplied to a processor (and/or other appropriate elements), as in FIG. 6. Similar such processing elements may at least partly direct the operations of the components of the sample processing module 110.

As above, in this example, the fluid flow pathway is indicated by thicker arrows, while communication pathways among elements are omitted for clarity. In addition, the components that contact the sample are indicated by a fill pattern.

Figure 8:
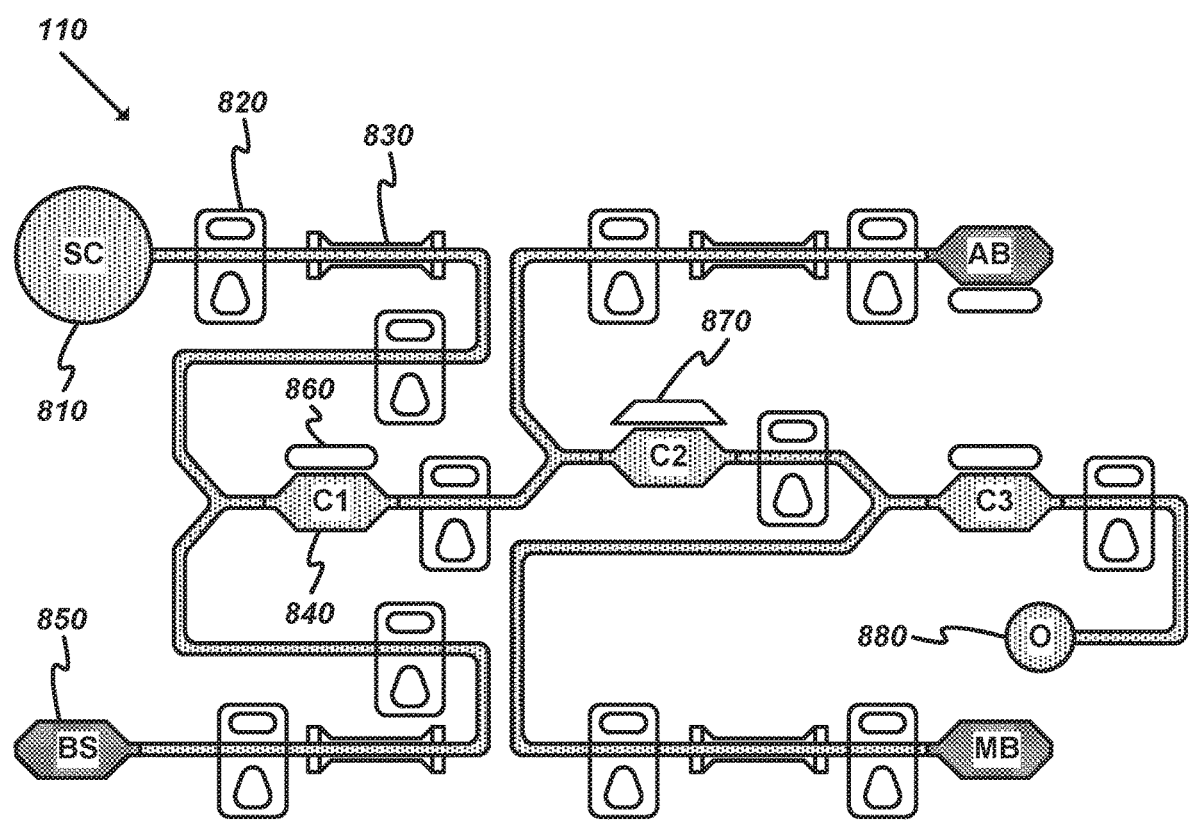
FIG. 8 illustrates a schematic block diagram of a third exemplary embodiment of the sample processing module included in the sample collection and testing device of FIG. 1.

FIG. 8 illustrates a schematic block diagram of a third exemplary embodiment of the sample processing module 110. As shown, the module may include a sample collection element 810, multiple volume measurement elements 820, multiple bi-directional pumps 830, multiple empty cavities 840, multiple pre-filled cavities 850, multiple detectors 860, at least one electromagnet 870, and a fluid output port 880.

The sample collection element 810 may be similar to element 605 described above. Each volume measurement element 820 may be similar to measurement elements 610-615 described above. In this example, measurement elements 820 are located throughout the module 110. Such an arrangement may be useful while developing or testing a new module or cartridge. Some embodiments may omit some such elements in order to reduce cost. Each bi-directional pump 830 may be similar to pumps 620-635 described above. The electromagnet 870 may be similar to electromagnet 660 described above.

Each empty cavity 840 may be similar to cavities 640-655 described above. Each pre-filled cavity 850 may be similar to cavities 640-655 described above and may include various solutions, materials, etc. that may be used during performance of the associated test. In this example, a first pre-filled cavity 850 includes a buffer solution (BS), a second pre-filled cavity includes electrically charged antibodies (AB), and a third pre-filled cavity includes certain agents or proteins attached to magnetic beads (MB). The size and/or other characteristics of each cavity 840-850 may depend on various relevant factors (e.g., desired volume, properties of stored solutions or materials, etc.).

Each detector 860 may be capable of detecting various attributes of the contents of an associated chamber 840 or 850. Such attributes may include, for instance, charge, impedance or conductance, pH level, color or other visual attributes, and/or any other measurable attribute of the fluid.

The fluid output port 880 may allow fluid to be provided to an external element via the cartridge of some embodiments. For instance, the cartridge may be removed and fluid collected from the cartridge for further analysis.

In this example, elements having a fill pattern are associated with a disposable portion of the module 110, while elements having no fill pattern are associated with the reusable portion of the module.

The outputs of the detectors 860 may be converted to a discrete value and supplied to a processor (and/or other appropriate elements), as in FIG. 6. Likewise, such elements may be able to at least partly direct the operations of the various pumps 830, measurement elements 820, sample collection element 810, detectors 860, electromagnet 870, etc.

Several sample operations of the sample processing modules of FIG. 6-FIG. 8 will be described in more detail in references to processes 1600-1800 below. In these examples, the sample collection modules may include similar (or the same) reusable components. For instance, although the different examples may include different numbers of cavities within the disposable cartridge, each example uses the same number of pumps (where the layout of each different cartridge may be arranged to utilize those pumps). Different embodiments may utilize different numbers of pumps (or other such reusable components) as well. In addition, the reusable components may include elements (e.g., the CL detector 700) that are only used by some embodiments of the disposable cartridge.

Figure 9:
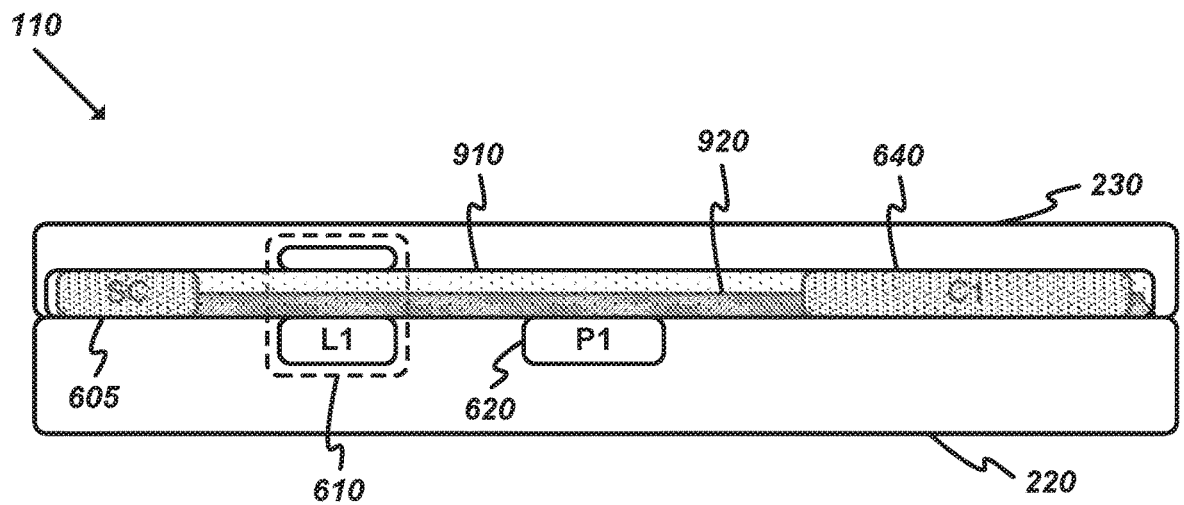
FIG. 9 illustrates a partial side view of a sample processing module according to an exemplary embodiment.

FIG. 9 illustrates a partial side view of a sample processing module 110 including a disposable cartridge 910 according to an exemplary embodiment. This example includes a sub-set of the components described above in reference to FIG. 6.

As shown, the sample processing module 110 of FIG. 9 may include the removable insert 910 including a fluid flow pathway 920, a top portion 230, and a bottom portion 220. In some embodiments, the top and bottom 220-230 may be reusable and may include a solid housing made of, for example, plastic or metal. The top and bottom may be coupled together (and/or to the device housing) in various appropriate ways, including hinges, latches, tabs and sockets, nuts and bolts, compression fit, magnets, etc.

The removable insert 910 may be made of (or housed within) a flexible material such as silicone such that inserts may be inserted into and/or removed from the cartridge housing. The insert may include various ridges, notches, slots, cavities, receptacles, etc. that may engage complementary elements of the cartridge housing.

Figure 10:
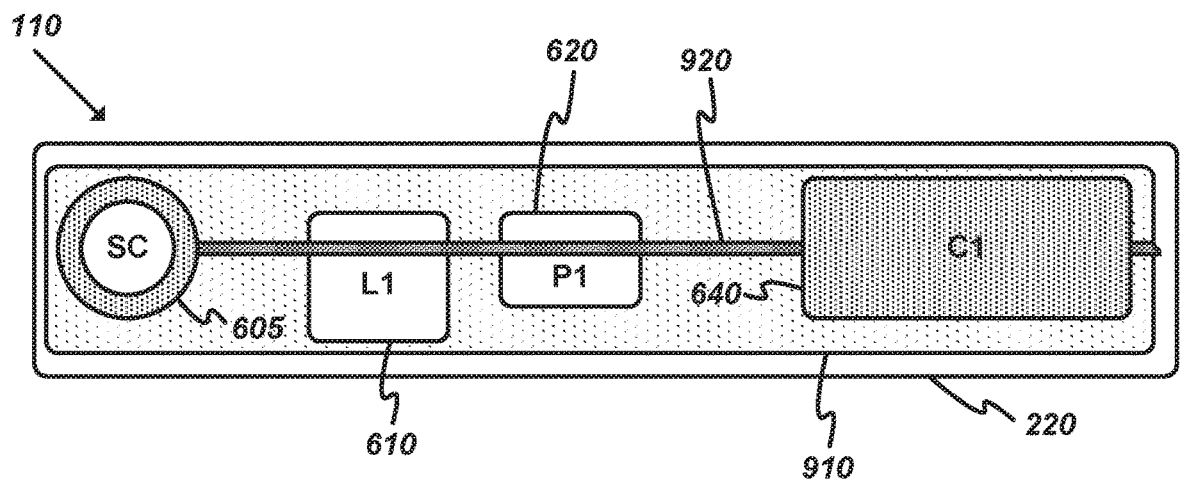
FIG. 10 illustrates a partial top view of a sample processing module according to an exemplary embodiment.

FIG. 10 illustrates a partial top view of a disposable insert 910 and sample processing module 110 according to an exemplary embodiment. This example includes the same sub-set of components shown in FIG. 9. In the view of FIG. 10, the top portion 230 has been omitted for clarity.

As shown, the disposable insert 910 may house at least a portion of the sample collection element 605, cavity 640, and cylindrical tubes or other appropriate connectors. The pump 620 may engage a portion of the flow pathway 920 without contacting the sample. For instance, the pump 620 may be a peristaltic pump that includes a rotating member with a number of protruding ridges aligned with a portion of the insert tubing 920. The optical measurement element 610 may be associated with a transparent or semitransparent portion of the insert 910 and associated tubing 920. The optical measurement element 910 may be oriented vertically, as in FIG. 9, horizontally, as in FIG. 10, and/or other may utilize other appropriate orientations.

Figure 11:
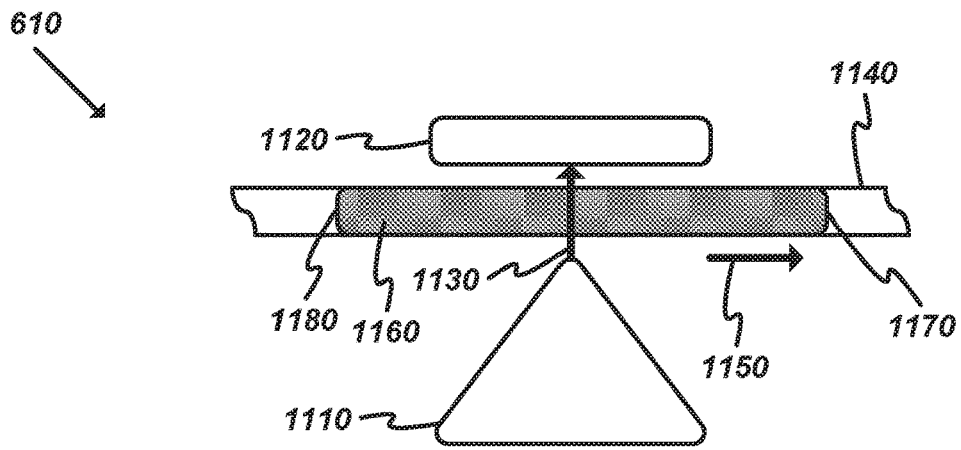
FIG. 11 illustrates a side elevation view of an optical measurement element according to an exemplary embodiment.

FIG. 11 illustrates a side elevation view of an optical measurement element 610 or 615 according to an exemplary embodiment. As shown, the optical measurement element may include an emitter 1110, an absorber 1120, a beam 1130, a fluid path 1140, forward flow direction 1150, fluid sample 1160, starting edge 1170, and ending edge 1180. The operation of the components of the optical measurement element 610 may be at least partly controlled by a resource such as controller 520.

At least some portions of the pathway 1140, including any portions associated with a beam 1130, may be translucent or semi-translucent such that more energy is able to be measured at the absorber 1120. When an opaque or semi-opaque fluid (such as blood) passes through that portion of the pathway 1140, the amount of energy measured at the absorber 1120 may decrease versus the energy absorbed when there is a lack of fluid in the pathway. An appropriate threshold may be set such that fluid flow at the particular location may be detected. The optical sensors 610 may be placed before and/or after an associated pump (and/or other appropriate components).

In this example, the emitter 1110 is on one side of the fluid path 1140 while the absorber 1120 is on an opposite side. The path 1140 may be embedded into an insert, such as path 920 in insert 910. In some embodiments, the emitter 1110 and absorber 1120 may both be on one side of the fluid path 1140 (e.g., both may be housed within the bottom portion 220 of the sample processing module 110), while a reflective element is located on the opposite side. Such embodiments may reduce the cost of components included in the disposable cartridge 240. In some embodiments, the absorber(s) 1120 may be located within the top portion 230 of the sample processing module.

Some embodiments may include other types of optical sensors. For instance, some embodiments may utilize an LED light source and a photodetector. The photodetector may have an analog output that is fed to an analog to digital converter for processing. Such a scheme may be used to measure volume by determining a length of fluid (e.g., one micron), and calculating a volume based on a diameter of a tube or other connecting element. The output of the photodetector may be analyzed by a processor to determine the beginning and end of a volume of fluid. Such an approach may allow very accurate measurement of volumes.

Some embodiments may capture, store, and/or analyze a signal that is generated based on the output of the photodetector or other absorbing element. Such an approach may allow the device to handle issues such as gaps in the fluid sample along the pathway. The signal may be stored (along with other test parameters) for future analysis.

In some embodiments, the detector 610 may measure a volume of fluid by incrementing a counter while the detector 610 senses an opaque fluid, where the count may be able to be translated to a fluid volume based on the sizing of the tubing 1140 and count duration. As each count increment may be associated with a very small amount of fluid, counting a large number of increments (e.g., five hundred, one thousand, etc.) may provide an accurate measure of volume.

One of ordinary skill in the art will recognize that the example architectures described above are exemplary in nature and different embodiments may be implemented in different specific ways without departing from the scope of the disclosure. For instance, various components may be combined or separated. As another example, various components may be distributed differently than shown (e.g., one or more pumps may be included in a disposable cartridge in some embodiments). As still another example, different embodiments may include different numbers of pumps, optical measurement elements, cavities, etc. Furthermore, different embodiments may be sized or shaped differently depending on the application. Such differences may include different layouts of internal components, circuitry, etc.

II. Methods of Operation

Figure 12:
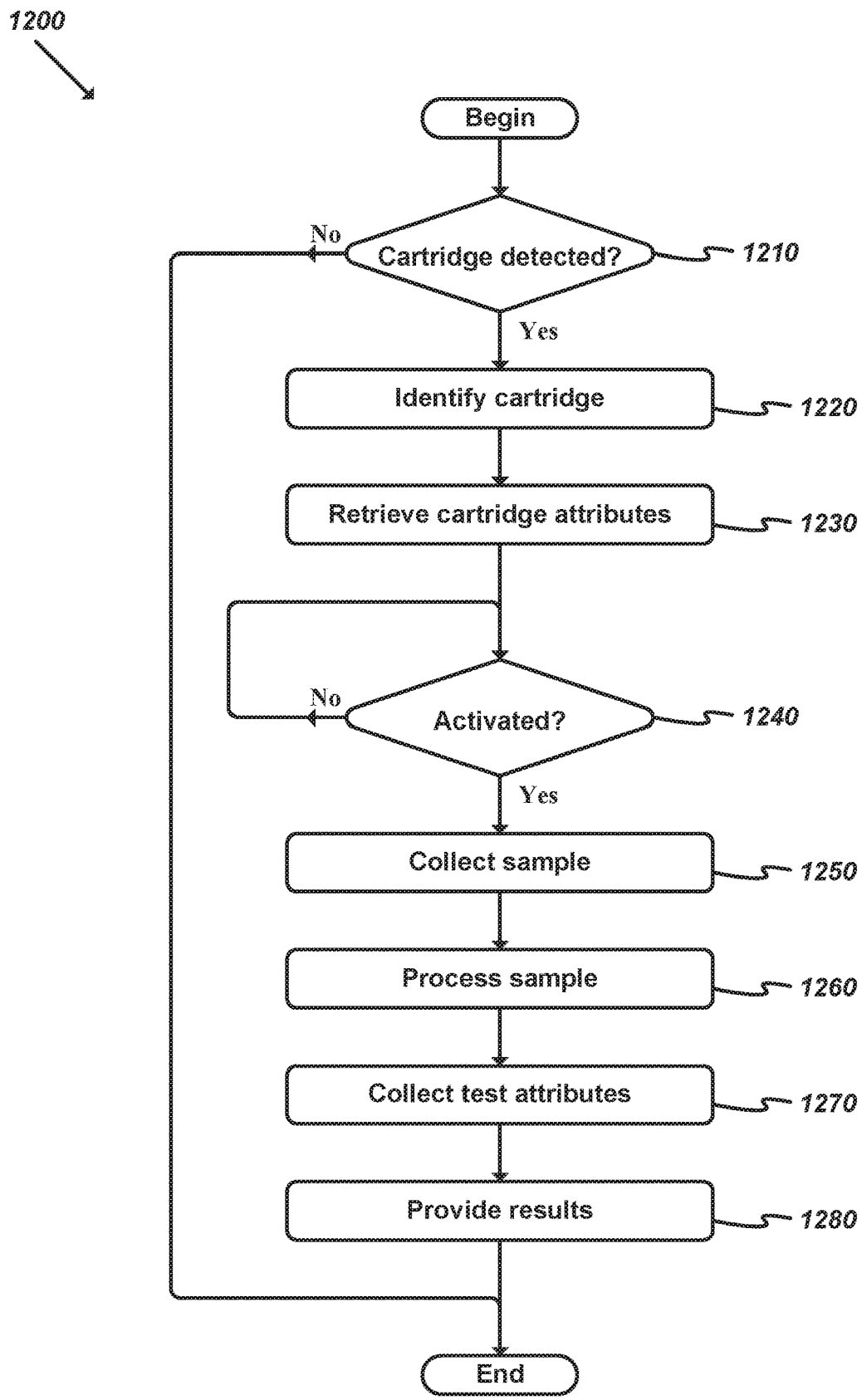
FIG. 12 illustrates a flow chart of an exemplary process that collects and tests a sample using the automated sample collection and testing device of FIG. 1.

FIG. 12 illustrates a flow chart of an exemplary process 1200 that collects and tests a sample using the automated SCTD 100. The process may begin when the device is powered on, when a sample processing module 110 is inserted, and/or other appropriate times.

As shown, the process may determine (at 1210) whether a cartridge is present. If the process determines that no cartridge is present, the process may end. If the process determines that a cartridge is present, the process may identify (at 1220) the cartridge. Such identification may include scanning of a graphic code, reading an RFID, receiving user input from an external device, etc.

Next, the process may retrieve (at 1230) cartridge attributes. Such attributes may be retrieved from the cartridge itself, from a local or remote database or look-up table, from user inputs, etc. The cartridge attributes may include, for instance, test type, fluid amounts (e.g., minimum sample volume), durations of operations (e.g., pulse counts associated with fluid measurements, reaction times, etc.), test or evaluation thresholds, etc.

The process may then determine (at 1240) whether the sample collection has been activated. Such a determination may be made based on various relevant factors, such as whether a finger (or other appropriate sample collection point) has been detected. Such a determination may be made using, for instance, the camera of some embodiments, a user input, a pressure sensor, etc.

If the process determines that no finger is detected, the process may continue trying to detect a finger until the process determines that a finger is detected. If the process determines that a finger is detected, the process may collect (at 1250) a sample. Such a sample may be collected using a needle and/or other appropriate elements as described above. Sample collection will be described in more detail in reference to process 1300 below.

Next, process 1200 may process (at 1260) the sample. Several example of such processing is described in more detail in reference to processes 1600-1800 below.

The process 1200 may then collect (at 1270) test attributes. Such attributes may include, for instance, charge difference at a pair of charge detectors, impedance or conductance of a sample (and/or processed sample), pH level, and/or any other measurable attribute of the fluid.

Next, the process may provide (at 1280) the results, and then may end. Such results may be based on comparison of the test attributes to one or more threshold values. The results may include discrete values (e.g., "pass", "fail", "inconclusive", etc.), measured values (e.g., weight or percentage of some tested parameter), and/or other appropriate result formats. The results may be provided via the SCTD 100 (e.g., using UI 120), a user device or medical device 510, and/or other appropriate ways. Some embodiments may send the results (and/or measure or intermediate values) to multiple external devices or systems using an element such as communication module 560.

Figure 13:
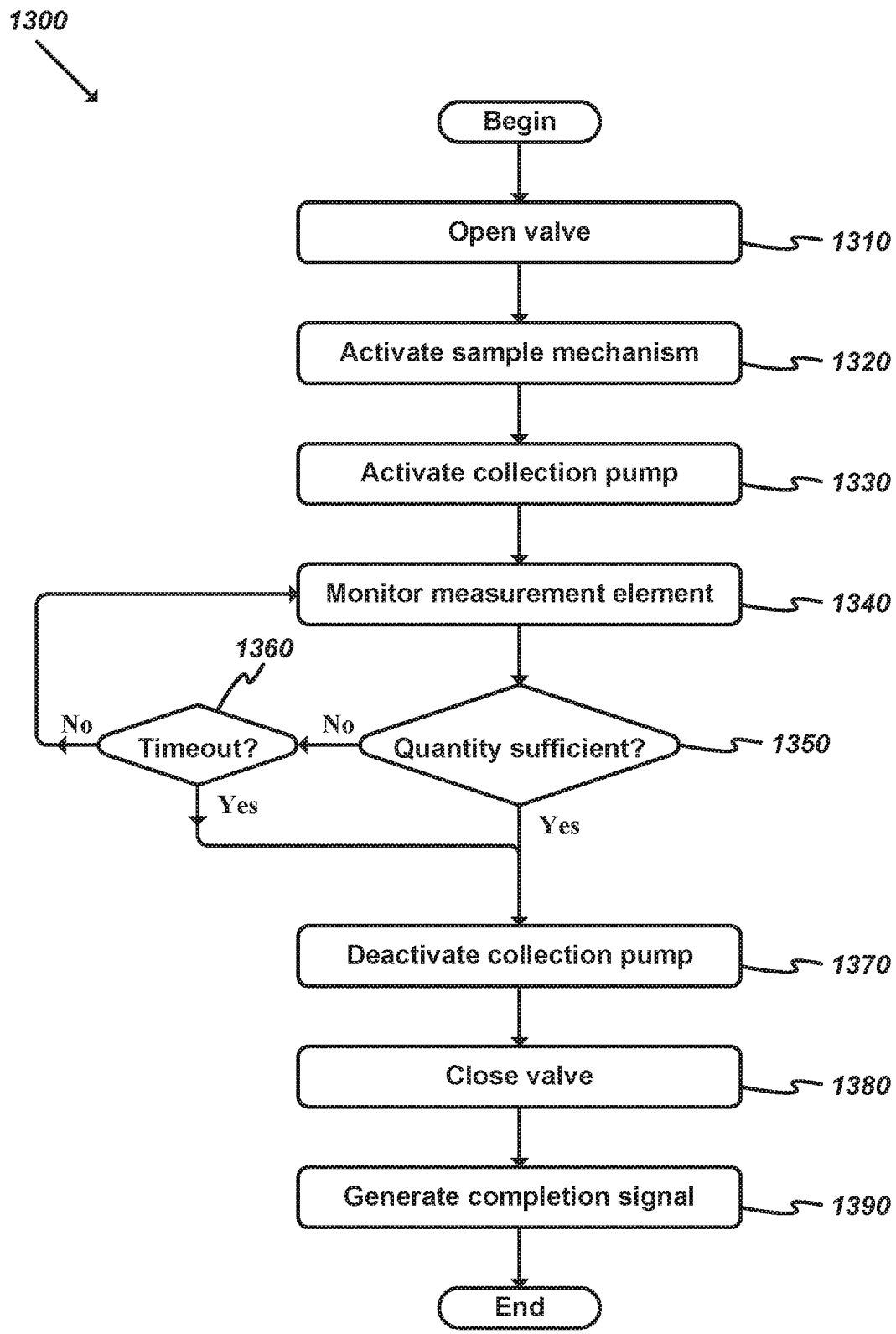
FIG. 13 illustrates a flow chart of an exemplary process that collects a sample using the automated sample collection and testing device of FIG. 1.

FIG. 13 illustrates a flow chart of an exemplary process 1300 that collects a sample using the automated SCTD 100. The process may begin when sample collection is activated as described in reference to operation 1240 above.

As shown, the process 1300 may open (at 1310) a valve such as pinch valve 320. Next, the process may activate (at 1320) a sample mechanism. Such a mechanism may include elements such as needle and spring 345, receptacle 340, and chip 325 described above. Activation of the sampling mechanism will be described in more detail in reference to process 1400 below.

Next, process 1300 may activate (at 1330) a collection pump, such as pump 315. The process may then monitor (at 1340) a measurement element such as element 610 described above. Alternatively, some embodiments may monitor collection using a camera, scale, etc. Some embodiments may simply utilize a timer rather than attributes associated with the sample itself.

The process may then determine (at 1350) whether the collected quantity is sufficient for the associated test. Such a determination may be made based on various relevant factors (e.g., counter value, weight of sample, etc.).

If the process determines the quantity is not sufficient, the process may then determine (at 1360) whether a sample timeout has been exceeded. If the process determines (at 1360) that the sample timeout has not been exceeded, the process may repeat operations 1340-1360 until the process determines (at 1350) that the quantity is sufficient or the process determines (at 1360) that the timeout has been exceeded.

If the process determines (at 1350) that the quantity is sufficient, or if the process determines (at 1360) that the sample timeout has been exceeded, the process may deactivate (at 1370) the collection pump, close (at 1380) the valve, generate (at 1390) a completion signal, and then end. The completion signal may be an internal signal that is relayed to an element such as controller 520 and may be used as a trigger to continue operations of process 1200 after collecting a sample at 1250. In some cases, no further processing may be performed after sample collection, and the completion signal may include indications at UI 120, via user device 510, and/or other appropriate signals.

In cases where the process determines (at 1360) that the timeout has been exceeded, the completion signal may indicate that the sample quantity is insufficient. Such a signal may cause the process to be re-run, or may provide a UI indication that the sample is insufficient and instruct the subject to insert another finger (or take other appropriate actions to successfully complete a sample collection, such as the insertion of a new cartridge).

Figure 14:
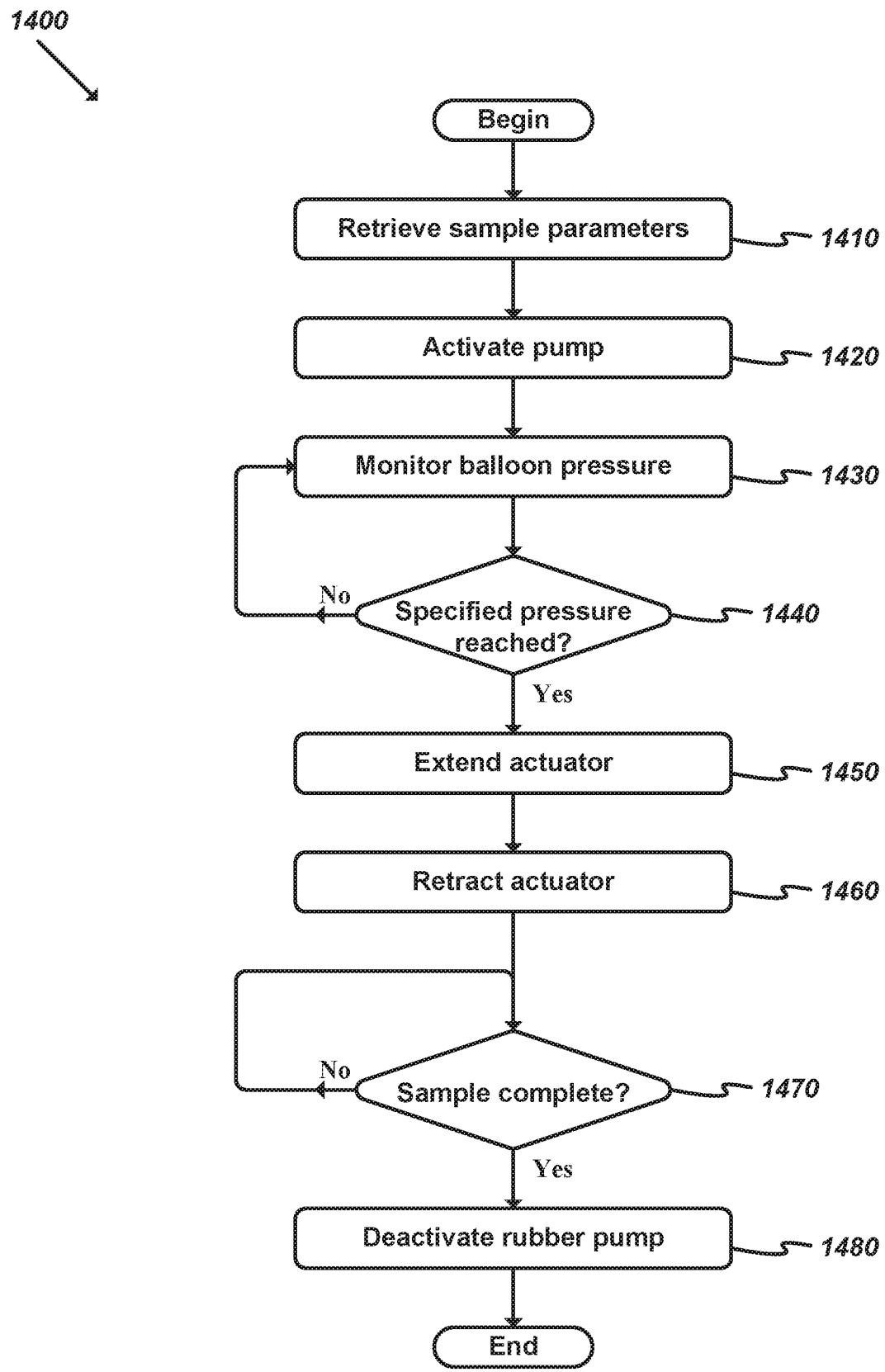
FIG. 14 illustrates a flow chart of an exemplary process that controls a sampling element of the automated sample collection and testing device of FIG. 1.

FIG. 14 illustrates a flow chart of an exemplary process 1400 that controls a sampling element of the automated SCTD 100. The process may begin when sample collection is activated as described in reference to operation 1320 above.

As shown, process 1400 may retrieve (at 1410) sample collection parameters. Such parameters may include, for instance, balloon pressure, needle extension, etc.

Next, the process may activate (at 1410) a pump such as rubber pump 305 and monitor (at 1430) pressure at a retaining element such as balloon 310. Next, the process may determine (at 1440) whether the specified pressure (or other parameter) has been reached. The process may repeat operations 1430-1440 until the process determines (at 1440) that the specified pressure has been reached.

Next, the process may extend (at 1450) an actuator such as actuator 335, such that the needle 345 or other sampling element is extended. The actuator may be extended to a specified value or may be full extended and limited by physical features of the needle, actuator housing, stops, etc.

The process may then retract (at 1460) the actuator and determine (at 1470) whether the sampling is complete. Such a determination may be made in various appropriate ways. For instance, some embodiments may wait for a completion message as described above in reference to operation 1390. As another example, some embodiments may wait for a specified amount of time. As still another example, some embodiments may wait for a user input to be received via a UI element, user device, medical device, etc.

If the process determines (at 1470) that the sample is complete, the process may deactivate (at 1480) the rubber pump (and/or other retaining elements) and then may end.

Figure 15:
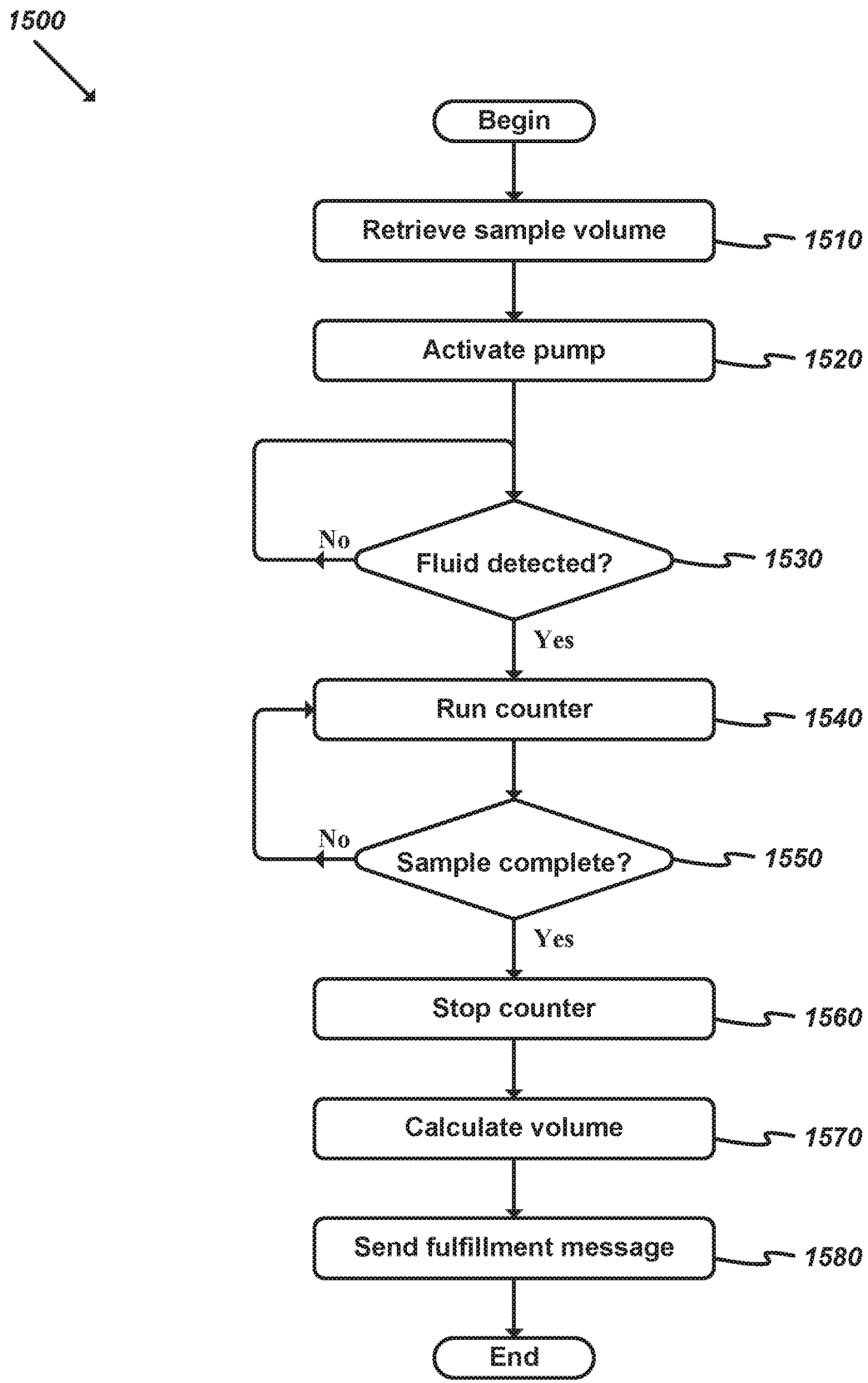
FIG. 15 illustrates a flow chart of an exemplary process that impels a small amount of fluid within the exemplary embodiments of the sample processing module included in the sample collection and testing device of FIG. 1.

FIG. 15 illustrates a flow chart of an exemplary process 1500 that impels a small amount of fluid within the exemplary embodiments of the sample processing module 110. Such a process may be executed by the SCTD 100 using an optical element such as element 610. The process may begin, for instance, when a sample is available or when a sample is being taken.

As shown, the process may retrieve (at 1510) a necessary (or minimum) sample volume. Such a volume may be retrieved from the cartridge, from a database or look-up table, received from a user, and/or other appropriate resource. The volume may be expressed as a count value or other discrete value associated with different measurement algorithms of different embodiments.

Next, the process may activate (at 1520) the appropriate pump associated with the measurement. Such a pump may be similar to pumps 315 or 620-635.

The process may then determine (at 1530) whether fluid is detected at the location of the flow pathway associated with the laser sensor 610 (and/or other appropriate elements). Such detection may be based on detection of a leading edge 1170 such as that described above. The process may iteratively or continuously attempt to detect fluid until the process determines that fluid has been detected, at which point, the process may activate (at 1540) a counter or other timing algorithm.

Such a counter may be a digital and/or analog timer. In some embodiments, the counter may specify a duration during which the fluid is detected. In other embodiments, the counter may specify a number of motor pulses to be applied (or a duration during which pulses are applied). The counter may be incremented at regular intervals (e.g., each clock period) when used to measure duration of time.

In some embodiments, as described above, the sensor 610 output may be converted to a digital or analog signal. In such cases, the signal may be analyzed in various appropriate ways in order to generate a "count" value (where such a value, in addition to being a literal counter or timer, may include any appropriate signal analysis). For instance, some embodiments may integrate the signal to calculate an area under a curve that may be used as the count value in order to determine a volume. As another example, the signal may be associated with various thresholds that may be used to activate or deactivate the counter (e.g., the counter value may increase when the signal is above a threshold and be held constant when the signal is below the threshold).

Next, the process may determine (at 1550) whether the sample is complete (i.e., whether the specified volume has been collected). Such a determination may be made based on whether a specified count threshold has been met or exceeded (and/or other appropriate analysis such as comparison of area to a threshold value).

If the process determines (at 1550) that the sample is not complete, the process may repeat operations 1540-1550 until the process determines (at 1550) that the sample is complete. In addition, the process may continue to monitor whether fluid is detected and may determine (at 1550) that the sample is complete when no more fluid is detected at the monitored portion of the fluid pathway. Such a determination may be made based on a gap in fluid detection having a minimum width or time duration, a sensor signal that drops below a specified threshold, etc.

If the process determines (at 1550) that the threshold volume has been collected, the process may stop (at 1560) the counter, deactivate (at 1570) the pump, send (at 1580) a completion message to other components or devices, and then may end.

Figure 16:
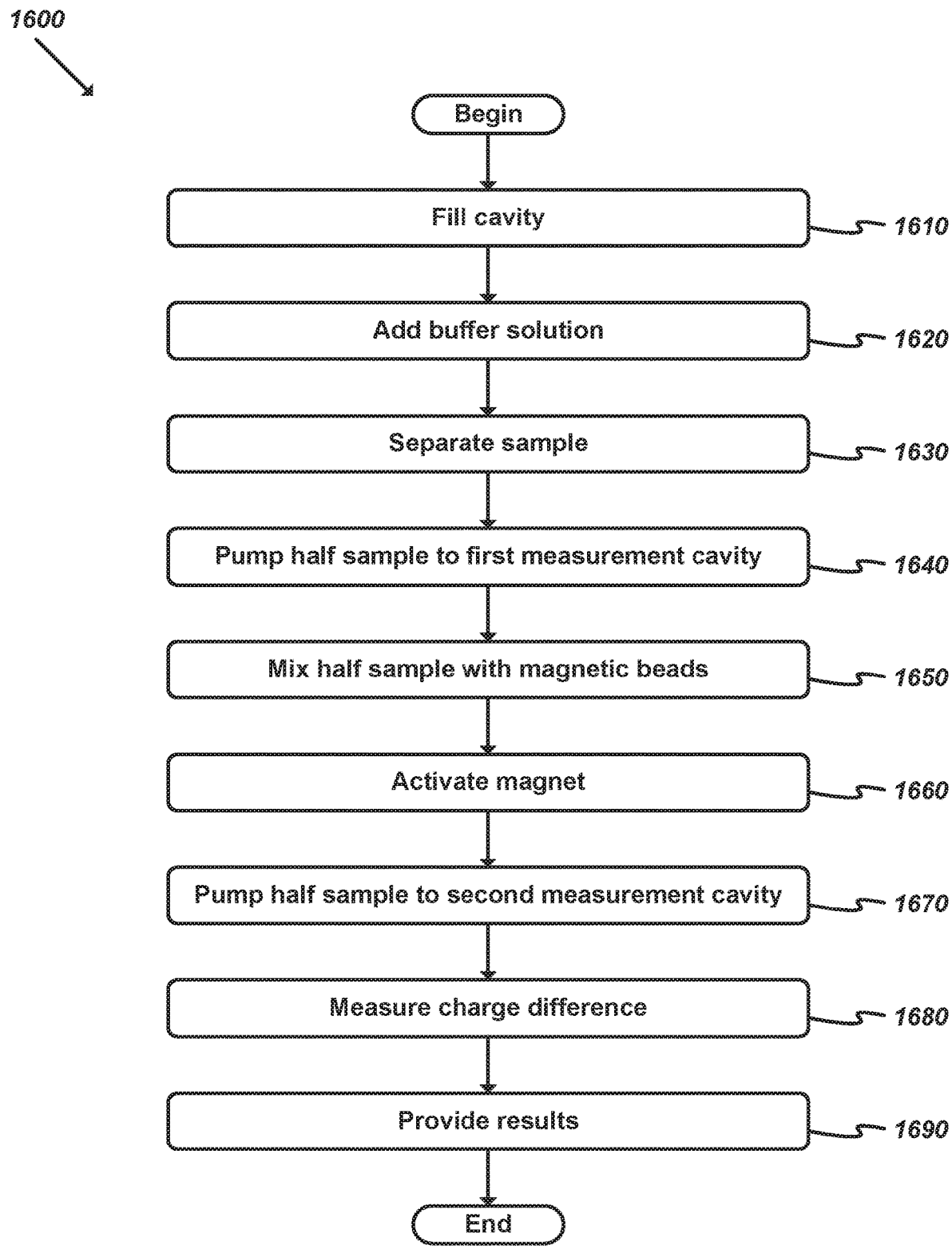
FIG. 16 illustrates a flow chart of an exemplary process that processes a sample using the sample processing module of FIG. 6.

FIG. 16 illustrates a flow chart of an exemplary process 1600 that processes a sample using the sample processing module 110 of FIG. 6. Such a process may be executed by the SCTD 100. The process may begin after a sample is taken, such as described above in reference to operation 1250 and process 1300.

As shown, process 1600 may fill (at 1610) a first cavity (e.g., cavity 640). Such a cavity may be filled using a first pump (e.g., pump 620) and a first laser sensor (e.g., sensor 610) to provide a specified amount of fluid to the cavity (e.g., cavity 640). Some embodiments may apply one thousand pulses, for example, to the pump in order to move one microliter of blood, with an accuracy of approximately one nanoliter.

In some embodiments, the optical sensor (e.g., sensor 610) may be placed before a pump (e.g., pump 620) such that when fluid is detected at the optical sensor, a stepper motor of the pump may be operated for a number of pulses in order to move a defined amount of fluid. Such sensor placement may result in improved accuracy by eliminating additional fluid that may be retained past the pump and later pulled into the associated cavity.

Next, the process may add (at 1620) a buffer solution. The buffer solution may be stored in a second cavity (e.g., cavity 645) and moved into the first cavity using a second pump (e.g., pump 625). The second pump may then be reversed and the mixture moved into the second cavity. Such operations may be performed over multiple iterations to thoroughly mix the solution.

The process may then separate (at 1630) the sample into halves (and/or other portion ratios). A third pump (e.g., pump 630) and second laser sensor (e.g., sensor 635) may be used to accurately measure the appropriate amount of fluid (whether half or some other ratio) and move (at 1640) that amount into a third cavity (e.g., cavity 650). The third cavity may include electrically charged HAAH antibodies (or any other appropriate antibody).

In addition, the second pump may be used to move (at 1640) the half sample in the second cavity to the first measurement cavity (e.g., cavity 640). The third pump may move the mixture in the third cavity between the third cavity and the second cavity to thoroughly mix the solution. At this point, any HAAH molecules in the blood sample will attach to the HAAH antibodies (or the target molecules will attach to other types of charged antibodies).

Next, the process may mix (at 1650) the half sample in the third cavity with the content of a fourth cavity (e.g., cavity 655) using a fourth pump (e.g., pump 635). The fourth cavity may include HAAH and magnetic beads that attach to any leftover HAAH antibodies that have not been attached to HAAH molecules in the blood.

The process may then activate (at 1660) the electromagnet. Next, the process may use the fourth pump to move (at 1670) the contents of the third cavity to the fourth cavity (or second measurement cavity), excluding the contents that are retained in the third cavity by the electromagnet.

The process may then measure (at 1680) the charge difference between the charge of the first cavity and the charge of the fourth cavity. The difference is proportional to the density of HAAH in the blood and may be provided as the final output of the process. After providing (at 1690) the results of the charge difference measurement, the process may end.

In addition, the results and/or other parameters (e.g., optical measurement waveforms, count values, subject information, test parameters, etc.) may be stored for future reference and analysis.

HAAH molecules (and HAAH antibodies) are described as one example only. Other embodiments may utilize various other antibodies such that the density of any target molecules in a sample may be determined.

Figure 17:
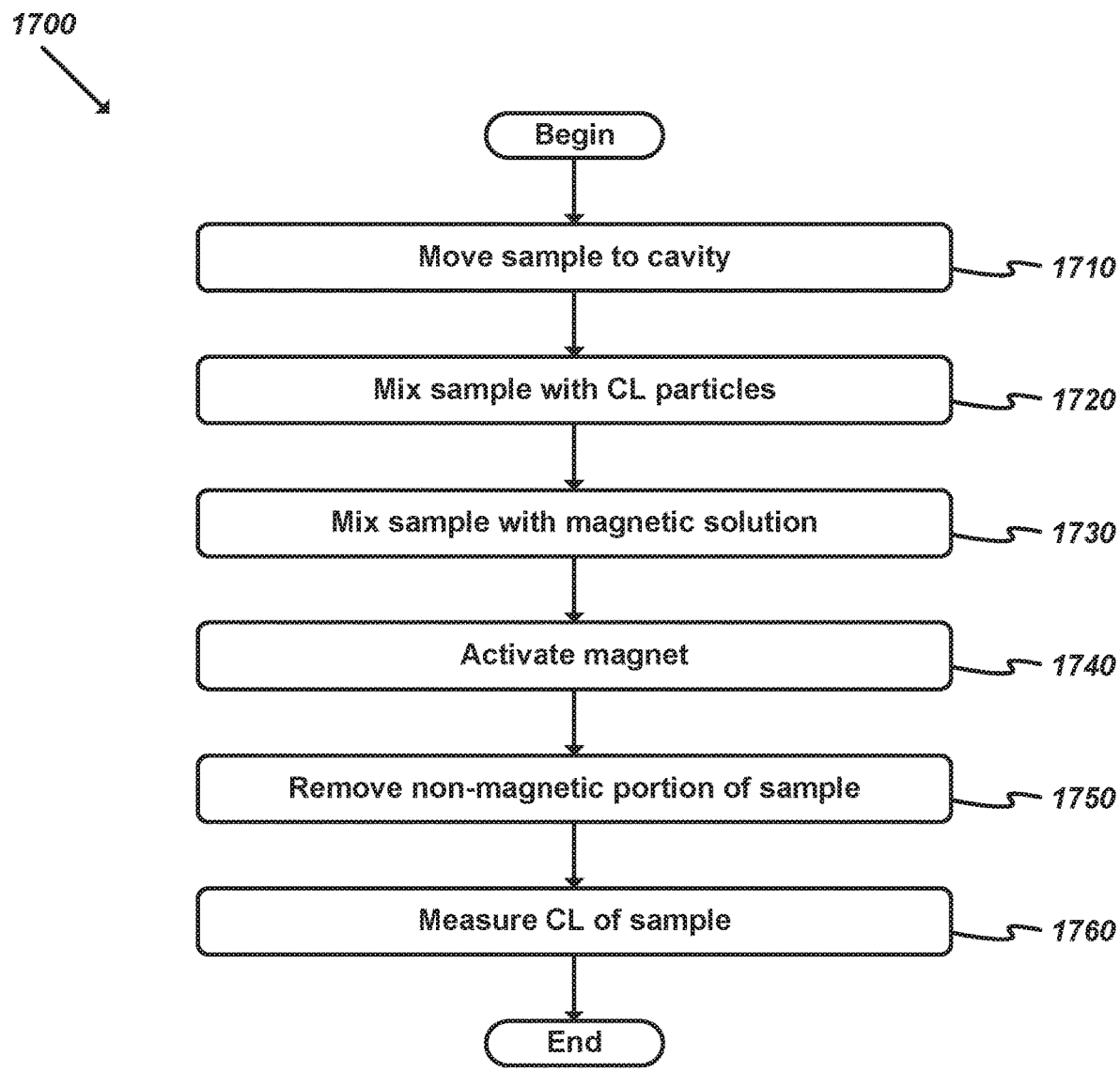
FIG. 17 illustrates a flow chart of an exemplary process that processes a sample using the sample processing module of FIG. 7.

FIG. 17 illustrates a flow chart of an exemplary process 1700 that processes a sample using the sample processing module of FIG. 7. Such a process may be executed by the SCTD 100.

The process may begin after a sample is taken, such as described above in reference to operation 1250 and process 1300.

As shown, process 1700 may move (at 1710) the sample to a first cavity such as cavity 640. Such a sample may be collected via sample collection element 605 and pump 620. The operations of the pump may be at least partly controlled based on data provided from a measurement element such as element 610. The first cavity may be pre-filled with a buffer solution.

Next, the process may mix (at 1720) the sample and buffer solution with a CL agent attached to an antibody (e.g., CL attached to HAAH antibody). A second cavity, such as cavity 645, may be pre-filled with such antibodies. A pump such as pump 625 may be used to mix the contents of the first and second cavities by moving the mixture between the cavities several times.

The process may then mix (at 1730) the sample with the complementary molecule attached to magnetic beads such as those described above (e.g., HAAH protein attached to magnetic beads). A third cavity (e.g., cavity 650) may be pre-filled with such a solution and the sample may be mixed using pump 630 to move the mixture between the second and third cavities.

Next, the process may activate (at 1740) the electromagnet (e.g., magnet 660) and then remove (at 1750) the non-magnetic portion of the sample mixture. The non-magnetic portion may be removed using pump 630, for instance, such that the non-magnetic portion (which includes the bound CL agents and antibodies) may be retained in the second cavity.

Finally, the process may measure (at 1760) the CL of the mixture in the second cavity and then may end. Such a measurement may be made using a detector such as detector 700 described above. The measurement may be provided to various appropriate resources, such as a processor, user device, etc. Likewise, the measurement may be provided by a UI 120 of some embodiments.

Figure 18:
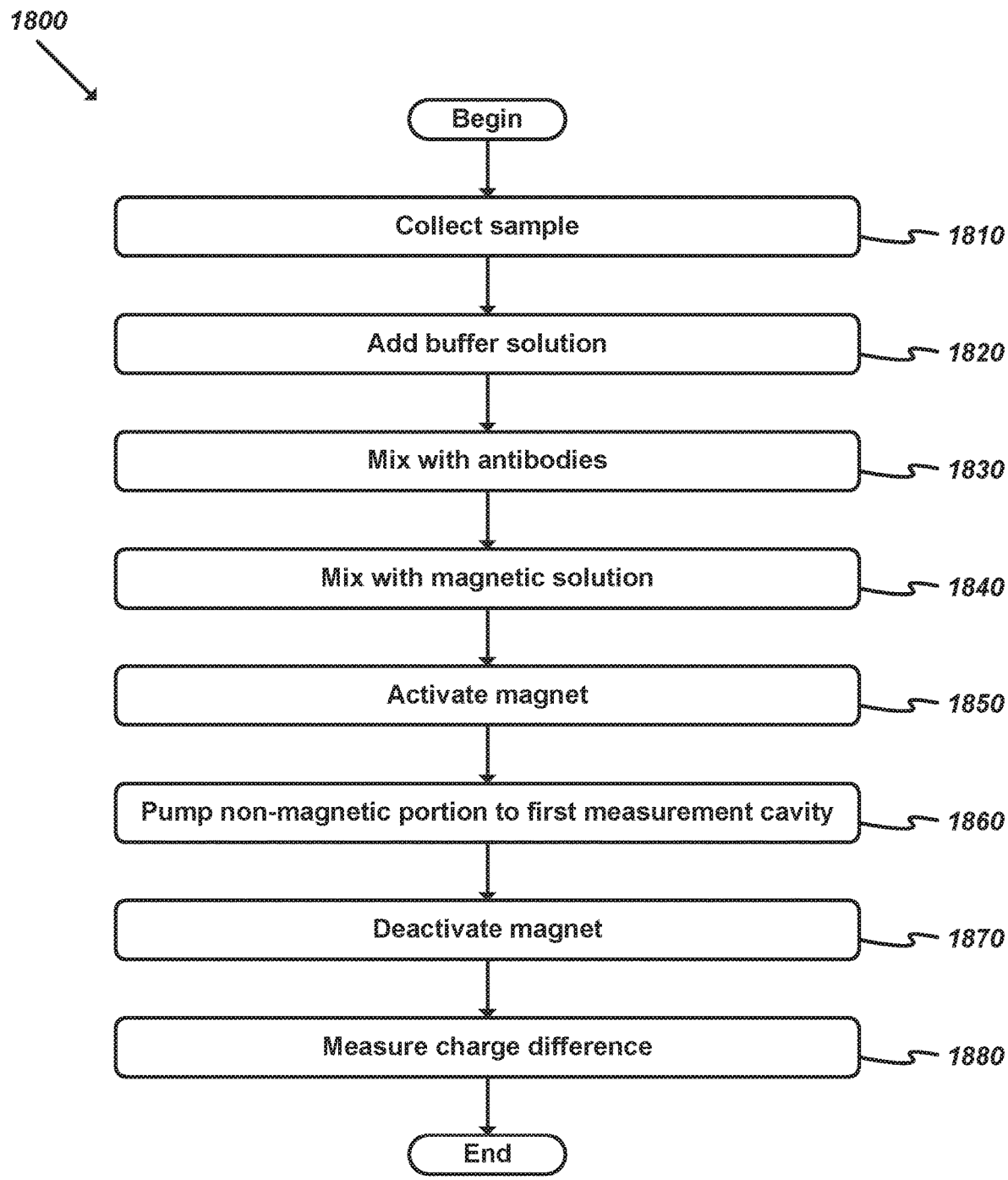
FIG. 18 illustrates a flow chart of an exemplary process that processes a sample using the sample processing module of FIG. 8.

FIG. 18 illustrates a flow chart of an exemplary process 1800 that processes a sample using the sample processing module 110 of FIG. 8. Such a process may be executed by the SCTD 100. The process may begin after a sample is taken, such as described above in reference to operation 1250 and process 1300.

As shown, process 1800 may collect (at 1810) a sample. Such a sample may be collected via sample collection element 810 using a first pump 830, first and second measurement elements 820, and a first cavity (C1) 840.

Next, the process may add (at 1820) a buffer solution to the sample. The buffer solution may be moved to the first cavity (C1) 840 using a second pump 830, third and fourth measurement elements 820, and a pre-filled cavity (BS) 850. As above, the solution may be moved between cavity (BS) and cavity (C1) several times to thoroughly mix the solution. Some portion of the mixture (usually 50%) may be retained in some embodiments (e.g., within cavity (C1)) for future analysis.

The process may then mix (at 1830) the mixture with electrically charged antibodies by moving a portion (usually 50%) of the contents of cavity (C1) to cavity (C2) while also moving the contents of cavity (AB) into cavity (C2) as well. The pre-filled cavity (AB) may include such antibodies, which may be mixed with the mixture of cavity (C1). The mixing of such elements may be performed using a combination of the pumps 830, where some pumps may act as valves at any given time while one or more pumps may be used to move the contents of various cavities along the fluid pathway to other cavities.

Next, the process may mix (at 1840) the mixture in cavity (C2) with a certain agent or protein (e.g., HAAH protein) attached to magnetic beads. Pre-filled cavity (MB) may include such a magnetic solution. The mixture may be retained in cavity (C2). The process may then activate (at 1850) the electromagnet 870 such that the magnetic beads (and associated particles) are retained in the cavity (C2).

Process 1800 may then pump (at 1860) the non-magnetic portion of the mixture in cavity (C2) to a third measurement cavity (C3). Next, the process may deactivate (at 1870) the magnet.

Finally, the process may measure (at 1880) the charge difference between the first measurement cavity (C1) and the third measurement cavity (C3) and then may end. Alternatively, different embodiments may perform various other measurements (e.g., charge, impedance or conductance, pH level, color or other visual attributes, and/or any other measurable attribute of the fluid).

The measured value may be provided to various appropriate resources, such as a processor 520, user device 510, etc.

One of ordinary skill in the art will recognize that processes 1200-1800 are exemplary in nature and different embodiments may perform such processes in various different ways. For instance, the various operations may be performed in different orders. As another example, some embodiments may include additional operations and/or omit various operations. Further, some embodiments may divide the processes into multiple sub-processes and/or combine multiple processes into a macro process. Some operations, and/or sets of operations may be performed iteratively, and/or based on some criteria other than those described above.

III. Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be able to perform functions and/or features that may be associated with various software elements described throughout.

Figure 19:
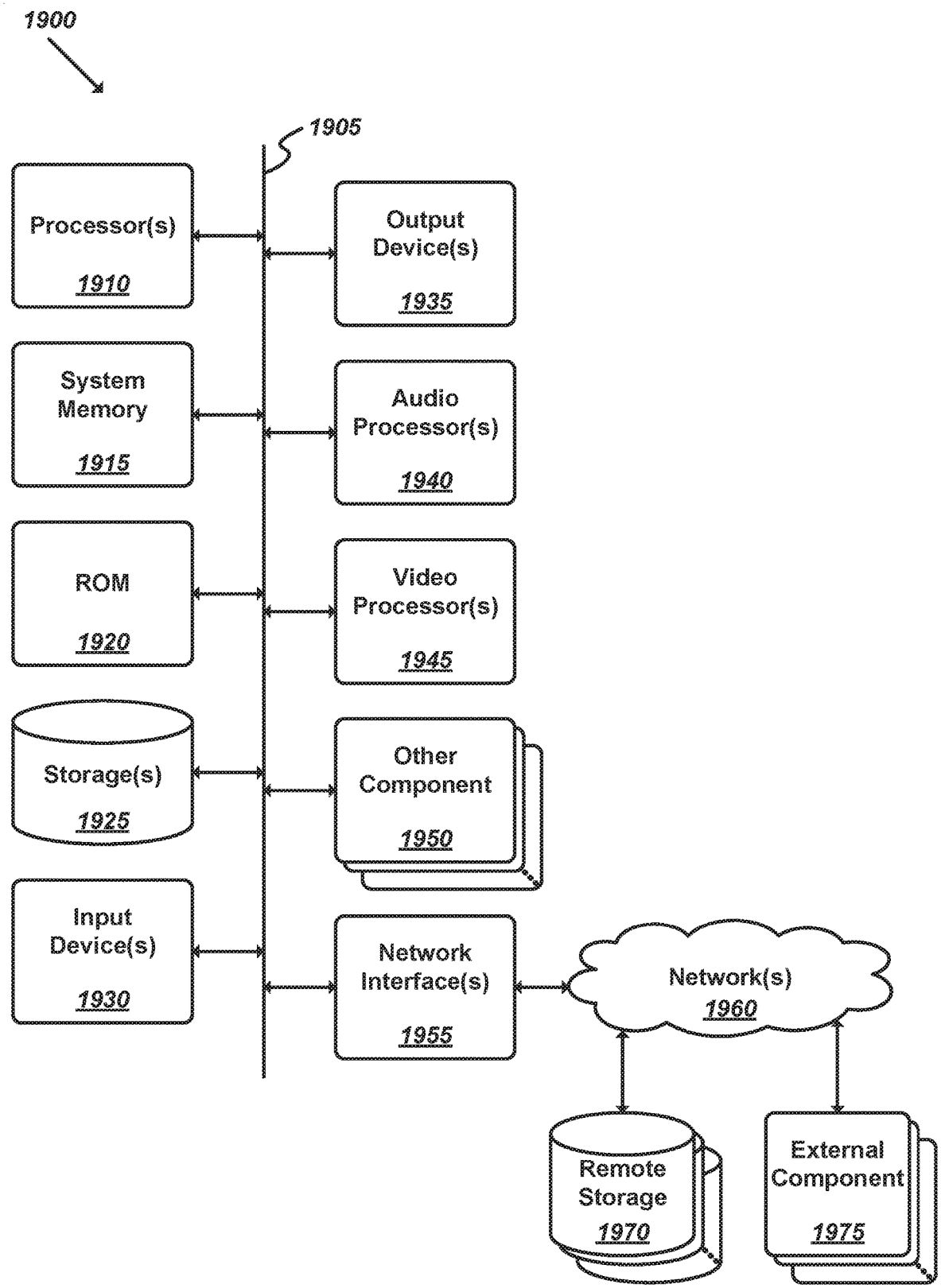
FIG. 19 illustrates a schematic block diagram of an exemplary computer system used to implement some embodiments.

FIG. 19 illustrates a schematic block diagram of an exemplary computer system 1900 used to implement some embodiments. For example, the system and devices described above in reference to FIG. 1-FIG. 11 may be at least partially implemented using computer system 1900. As another example, the processes described in reference to FIG. 12-FIG. 18 may be at least partially implemented using sets of instructions that are executed using computer system 1900.

Computer system 1900 may be implemented using various appropriate devices. For instance, the computer system may be implemented using one or more personal computers (PCs), servers, mobile devices (e.g., a smartphone), tablet devices, and/or any other appropriate devices. The various devices may work alone (e.g., the computer system may be implemented as a single PC) or in conjunction (e.g., some components of the computer system may be provided by a mobile device while other components are provided by a tablet device).

As shown, computer system 1900 may include at least one communication bus 1905, one or more processors 1910, a system memory 1915, a read-only memory (ROM) 1920, permanent storage devices 1925, input devices 1930, output devices 1935, audio processors 1940, video processors 1945, various other components 1950, and one or more network interfaces 1955.

Bus 1905 represents all communication pathways among the elements of computer system 1900. Such pathways may include wired, wireless, optical, and/or other appropriate communication pathways. For example, input devices 1930 and/or output devices 1935 may be coupled to the system 1900 using a wireless connection protocol or system.

The processor 1910 may, in order to execute the processes of some embodiments, retrieve instructions to execute and/or data to process from components such as system memory 1915, ROM 1920, and permanent storage device 1925. Such instructions and data may be passed over bus 1905.

System memory 1915 may be a volatile read-and-write memory, such as a random access memory (RAM). The system memory may store some of the instructions and data that the processor uses at runtime. The sets of instructions and/or data used to implement some embodiments may be stored in the system memory 1915, the permanent storage device 1925, and/or the read-only memory 1920. ROM 1920 may store static data and instructions that may be used by processor 1910 and/or other elements of the computer system.

Permanent storage device 1925 may be a read-and-write memory device. The permanent storage device may be a non-volatile memory unit that stores instructions and data even when computer system 1900 is off or unpowered. Computer system 1900 may use a removable storage device and/or a remote storage device as the permanent storage device.

Input devices 1930 may enable a user to communicate information to the computer system and/or manipulate various operations of the system. The input devices may include keyboards, cursor control devices, audio input devices and/or video input devices. Output devices 1935 may include printers, displays, audio devices, etc. Some or all of the input and/or output devices may be wirelessly or optically connected to the computer system 1900.

Audio processor 1940 may process and/or generate audio data and/or instructions. The audio processor may be able to receive audio data from an input device 1930 such as a microphone. The audio processor 1940 may be able to provide audio data to output devices 1940 such as a set of speakers. The audio data may include digital information and/or analog signals. The audio processor 1940 may be able to analyze and/or otherwise evaluate audio data (e.g., by determining qualities such as signal to noise ratio, dynamic range, etc.). In addition, the audio processor may perform various audio processing functions (e.g., equalization, compression, etc.).

The video processor 1945 (or graphics processing unit) may process and/or generate video data and/or instructions. The video processor may be able to receive video data from an input device 1930 such as a camera. The video processor 1945 may be able to provide video data to an output device 1940 such as a display. The video data may include digital information and/or analog signals. The video processor 1945 may be able to analyze and/or otherwise evaluate video data (e.g., by determining qualities such as resolution, frame rate, etc.). In addition, the video processor may perform various video processing functions (e.g., contrast adjustment or normalization, color adjustment, etc.). Furthermore, the video processor may be able to render graphic elements and/or video.

Other components 1950 may perform various other functions including providing storage, interfacing with external systems or components, etc.

Finally, as shown in FIG. 19, computer system 1900 may include one or more network interfaces 1955 that are able to connect to one or more networks 1960. For example, computer system 1900 may be coupled to a web server on the Internet such that a web browser executing on computer system 1900 may interact with the web server as a user interacts with an interface that operates in the web browser. Computer system 1900 may be able to access one or more remote storages 1970 and one or more external components 1975 through the network interface 1955 and network 1960. The network interface(s) 1955 may include one or more application programming interfaces (APIs) that may allow the computer system 1900 to access remote systems and/or storages and also may allow remote systems and/or storages to access computer system 1900 (or elements thereof).

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

It should be recognized by one of ordinary skill in the art that any or all of the components of computer system 1900 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The foregoing relates to illustrative details of exemplary embodiments and modifications may be made without departing from the scope of the disclosure as defined by the following claims.

I claim:

1. An automated fluid sample collector comprising:
    a collection receptacle;
    a user interface (UI) element;
    a controllable electronic actuator having configurable attributes including depth and acceleration;

a controller that receives user input data from the UI element and at least partly directs the operations of the controllable electronic actuator such that the configurable attributes including depth and acceleration are based at least partly on the user input data;

a piercing element coupled to the controllable electronic actuator;

a silicone chip comprising a fluid storage cavity and a fluid flow pathway, wherein the fluid storage cavity is coupled to the collection receptacle via the fluid flow pathway; and a pump associated with the fluid flow pathway, wherein the pump:
- moves fluid along the fluid flow pathway in a first operating state,
- forms a pinch valve that prevents movement of fluid along the fluid flow pathway in a second operating state, and
- engages an outer surface of the silicone chip such that the pump does not physically contact fluid housed by the fluid flow pathway.

2. The automated fluid sample collector of claim 1, wherein the collection receptacle comprises a fluid test strip.

3. The automated fluid sample collector of claim 1, wherein the piercing element comprises a needle.

4. The automated fluid sample collector of claim 1 further comprising a retaining element able to secure a subject to the collection receptacle.

5. The automated fluid sample collector of claim 1 further comprising a communication module able to communicate with a user device across a wireless channel, wherein at least one of the configurable attributes is specified based on information received via the communication module.

6. An automated sample collection device comprising:
a sample receptacle;
a needle that is able to extend into the sample receptacle;
a controllable actuator coupled to the needle such that the controllable actuator extends and retracts the needle, the controllable actuator having configurable attributes including depth and acceleration;
a controller that receives user input data from at least one of a user interface element and a communication interface communicatively coupled to a user device and that at least partly directs the operations of the controllable electronic actuator such that the configurable attributes including depth and acceleration are based at least partly on the user input data;
a silicone fluid chip coupled to the sample receptacle, the silicone fluid chip comprising a fluid storage cavity able to accommodate an amount of collected fluid and a fluid flow pathway, wherein the fluid storage cavity is coupled to the sample receptacle via the fluid flow pathway; and
a pump associated with the fluid flow pathway, wherein the pump:
- moves fluid along the fluid flow pathway in a first operating state,
- forms a pinch valve that prevents movement of fluid along the fluid flow pathway in a second operating state, and
- engages an outer surface of the silicone fluid chip such that the pump does not physically contact the collected fluid.

7. The automated sample collection device of claim 6 further comprising a retaining element able to secure a subject with respect to the sample receptacle.

8. The automated sample collection device of claim 7, wherein the retaining element comprises a retaining pump and a balloon and is able to secure a finger with respect to the sample receptacle.

9. The automated sample collection device of claim 6 further comprising an optical fluid meter able to measure the amount of collected fluid.

10. The automated sample collection device of claim 6, wherein a portion of the silicone fluid chip comprises self-sealing material and the needle passes through the portion of the silicone fluid chip.

11. The automated sample collection device of claim 6 further comprising a communication module able to communicate with a user device across a wireless channel, wherein at least one of the configurable attributes is specified based on information received via the communication module.

* * * * *